(12) United States Patent
Baudry et al.

(10) Patent No.: US 8,642,559 B2
(45) Date of Patent: Feb. 4, 2014

(54) C-TERMINAL DOMAIN TRUNCATION OF MGLUR1α BY CALPAIN AND USES THEREOF

(75) Inventors: Michel Baudry, Irvine, CA (US); Wei Xu, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 844 days.

(21) Appl. No.: 12/443,157

(22) PCT Filed: Oct. 12, 2007

(86) PCT No.: PCT/US2007/021806
§ 371 (c)(1),
(2), (4) Date: Feb. 9, 2010

(87) PCT Pub. No.: WO2008/063315
PCT Pub. Date: May 29, 2008

(65) Prior Publication Data
US 2010/0144623 A1    Jun. 10, 2010

Related U.S. Application Data

(60) Provisional application No. 60/829,428, filed on Oct. 13, 2006.

(51) Int. Cl.
*C07K 7/00* (2006.01)
(52) U.S. Cl.
USPC .......................................... 514/21.5; 530/327

(58) Field of Classification Search
USPC ......................................... 514/21.5; 530/327
See application file for complete search history.

(56) References Cited

U.S. PATENT DOCUMENTS 5,385,831 A * 1/1995 Mulvihill et al. ............ 435/69.1
2008/0234183 A1 * 9/2008 Hallbrink et al. ............... 514/12

OTHER PUBLICATIONS

Bartus, et al., Stroke 25(11):2265-2270, (1994).
Goll, et al., Physiol Rev 83(3):731-801, 2003.
Liebetrau, et al., Neurol Res 27(5):466-470, 2005.
Markgraf, et al., Stroke 29(1):152-158, 1998.
Wu, et al., Mol Neurobiol 33(3):215-236, 2006.

* cited by examiner

*Primary Examiner* — David Lukton
(74) *Attorney, Agent, or Firm* — DLA Piper LLP (US)

(57) ABSTRACT

A composition comprising a peptide or a peptidomimetic thereof that inhibits the C-terminal domain truncation of mGluR1α by calpain, wherein the peptide is 10-30 amino acids in length and contains a sequence that is at least 70% homologous to VIKPLTKSYQGSGK. Also disclosed are methods of detecting the C-terminal domain truncation of mGluR1α by calpain, methods of inhibiting the C-terminal domain truncation of mGluR1α in a neuron, and methods of identifying a compound that inhibits the C-terminal domain truncation of mGluR1α.

9 Claims, 13 Drawing Sheets

SEQUENCE LISTING

<160> NUMBER OF SEQ ID NOS: 10

<210> SEQ ID NO 1
<211> LENGTH: 14
<212> TYPE: PRT
<213> ORGANISM: Artificial Sequence
<220> FEATURE:
<223> OTHER INFORMATION: chemically synthesized peptide

<400> SEQUENCE: 1

Val Ile Lys Pro Leu Thr Lys Ser Tyr Gln Gly Ser Gly Lys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: chemically synthesized peptide

<400> SEQUENCE: 2

Val Ile Lys Pro Leu Thr Lys Gly Gly Gln Gly Ser Gly Lys
1               5                   10

<210> SEQ ID NO 3
<211> LENGTH: 14

```
<212> TYPE: PRT
<213> ORGANISM: Artificial Sequence
<220> FEATURE:
<223> OTHER INFORMATION: chemically synthesized peptide
<220> FEATURE:
<221> NAME/KEY: D-serine
<222> LOCATION: (8)..(8)
<220> FEATURE:
<221> NAME/KEY: D-tyrosine
<222> LOCATION: (9)..(9)

<400> SEQUENCE: 3

Val Ile Lys Pro Leu Thr Lys Xaa Xaa Gln Gly Ser Gly Lys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: chemically synthesized peptide
<220> FEATURE:
<221> NAME/KEY: D-alanine
<222> LOCATION: (8)..(8)
<220> FEATURE:
<221> NAME/KEY: D-phenylalanine
<222> LOCATION: (9)..(9)

<400> SEQUENCE: 4

Val Ile Lys Pro Leu Thr Lys Xaa Xaa Gln Gly Ser Gly Lys
1               5                   10

<210> SEQ ID NO 5
<211> LENGTH: 25
<212> TYPE: PRT
<213> ORGANISM: Artificial Sequence
<220> FEATURE:
<223> OTHER INFORMATION: chemically synthesized peptide

<400> SEQUENCE: 5

Tyr Gly Arg Lys Lys Arg Arg Gln Arg Arg Val Ile Lys Pro Leu
1               5                   10                  15

Thr Lys Ser Tyr Gln Gly Ser Gly Lys
            20                  25

<210> SEQ ID NO 6
<211> LENGTH: 25
<212> TYPE: PRT
<213> ORGANISM: Artificial Sequence
<220> FEATURE:
<223> OTHER INFORMATION: chemicallly synthesized peptide

<400> SEQUENCE: 6

Arg Arg Arg Gln Arg Arg Lys Lys Arg Gly Tyr Val Ile Lys Pro Leu
1               5                   10                  15

Thr Lys Ser Tyr Gln Gly Ser Gly Lys
            20                  25

<210> SEQ ID NO 7
<211> LENGTH: 25
<212> TYPE: PRT
<213> ORGANISM: Artificial Sequence
<220> FEATURE:
<223> OTHER INFORMATION: chemically synthesized peptide

<400> SEQUENCE: 7

Val Ile Lys Pro Leu Thr Lys Ser Tyr Gln Gly Ser Gly Lys Tyr Gly
1               5                   10                  15
```

-continued

```
Arg Lys Lys Arg Arg Gln Arg Arg
            20              25

<210> SEQ ID NO 8
<211> LENGTH: 27
<212> TYPE: PRT
<213> ORGANISM: Artificial Sequence
<220> FEATURE:
<223> OTHER INFORMATION: chemically synthesized peptide

<400> SEQUENCE: 8

Cys Tyr Gly Arg Lys Lys Arg Arg Gln Arg Arg Arg Cys Val Ile Lys
1               5                   10                  15

Pro Leu Thr Lys Ser Tyr Gln Gly Ser Gly Lys
            20                  25

<210> SEQ ID NO 9
<211> LENGTH: 11
<212> TYPE: PRT
<213> ORGANISM: Artificial Sequence
<220> FEATURE:
<223> OTHER INFORMATION: chemically synthesized peptide

<400> SEQUENCE: 9

Tyr Gly Arg Lys Lys Arg Arg Gln Arg Arg
1               5                   10

<210> SEQ ID NO 10
<211> LENGTH: 10
<212> TYPE: PRT
<213> ORGANISM: Artificial Sequence
<220> FEATURE:
<223> OTHER INFORMATION: chemically synthesized peptide

<400> SEQUENCE: 10

Glu Gln Lys Leu Ile Ser Glu Glu Asp Leu
1               5                   10
```

C-TERMINAL DOMAIN TRUNCATION OF MGLUR1α BY CALPAIN AND USES THEREOF

RELATED APPLICATION

This application is a national stage of international application No. PCT/US2007/021806 filed Oct. 12, 2007, which also claims the benefit of priority under 35 USC 119 to U.S. Patent Application Ser. No. 60/829,428 filed Oct. 13, 2006, the entire contents, all of which are incorporated herein by reference.

STATEMENT REGARDING FEDERALLY SPONSORED RESEARCH OR DEVELOPMENT

This invention was made with government support under Contract No. NS048521. The government has certain rights in the invention.

FIELD OF THE INVENTION

The present invention relates generally to methods of treating neurological injuries and neurodegenerative disorders. More particularly, the inventive methods include a novel approach for controlling excitotoxicity by blocking C-terminal domain truncation of mGluR1 receptors. The present invention also relates to novel pharmacological agents for controlling excitotoxicity, and methods for identifying and designing such agents.

BACKGROUND OF THE INVENTION

Neurological disorders such as stroke, multiple sclerosis (MS), Alzheimer's disease, Amyotrophic lateral sclerosis (ALS), Fibromyalgia (Smith et al., Ann Pharmacother 35(6): 702-706, 2001), Parkinson's disease, and Huntington's disease (Kim et al., Chapter 1 in CNS Neuroprotection. Springer, N.Y. pp. 3-36, 2002), eye pathologies, and traumatic brain injuries affect a large portion of the population, but efficient pharmacological treatments are still lacking. One crucial mechanism underlying these diseases is excitotoxicity conveyed by NMDA-type of glutamate receptors (NMDAR). Recent research has shown that this mechanism offers great potential for the development of new pharmacological treatments.

The term excitotoxicity refers to the pathological process by which neurons are damaged and killed by the overactivation of receptors for the excitatory neurotransmitter glutamate, such as the NMDA receptor and AMPA receptor. Excitotoxins like NMDA and kainic acid (KA) which bind to these receptors, as well as pathologically high levels of glutamate, can cause excitotoxicity by allowing high levels of calcium ions to enter the cell (Manev et al., Mol Pharmacol 36(1):106-112, 1989). $Ca^{++}$ influx into cells activates a number of enzymes, including phospholipases, endonucleases, and proteases such as calpain. Activation of these enzymes leads to irreversible damage to various cell structures such as components of the cytoskeleton, membranes, and DNA.

The neurotoxic effects of glutamate were first observed in 1954 by T. Hayashi, a Japanese scientist who noted that direct application of glutamate to the CNS caused seizure activity, though this report went unnoticed for several years. The toxicity of glutamate was then observed by D. R. Lucas and J. P. Newhouse in 1957 when the feeding of monosodium glutamate to newborn mice destroyed the neurons in the inner layers of the retina (Lucas et al., AMA Arch Ophthalmol 58(2):193-201, 1957). Later, in 1969, John Olney discovered the phenomenon wasn't restricted to the retina but occurred throughout the brain and coined the term excitotoxicity. He also assessed that cell death was restricted to postsynaptic neurons, that glutamate agonists were as neurotoxic as their efficiency to activate glutamate receptors, and that glutamate antagonists could stop the neurotoxicity (Olney, Science 164 (880):719-721, 1969).

The major excitotoxin in the brain, glutamate, is paradoxically also the major excitatory neurotransmitter in the mammalian CNS (Temple et al., Chapter 4 in Head Trauma: Basic, Preclinical, and Clinical Directions. John Wiley and Sons, Inc., New York. pp. 87-113, 2001). During normal synaptic transmission, glutamate concentration can be increased up to 1 mM in the synaptic cleft, which is rapidly decreased in the lapse of milliseconds. When the glutamate concentration around the synaptic cleft cannot be decreased or reaches higher levels, the overexcited neuron kills itself by a process called apoptosis; alternatively a necrosis cell death can also occur. This pathologic phenomenon is also frequently found after brain injury.

In brain trauma, or stroke, ischemia often results, reducing blood flow to inadequate levels. Ischemia is then followed by accumulation of glutamate and aspartate in the extracellular fluid, causing cell death, which is aggravated by the lack of oxygen and glucose. The biochemical cascade resulting from ischemia and involving excitotoxicity is called the ischemic cascade. Once the ischemic cascade triggers excitotoxicity, an influx of $Ca^{++}$ ensues to activate a number of cell damaging enzymes.

Another damaging result of excess calcium in the cytosol is the opening of the mitochondrial permeability transition pore, a pore in the membrane of mitochondria that opens when the organelles absorb too much calcium. Opening of the pore causes mitochondria to swell and release proteins that can lead to apoptosis. The pore can also cause mitochondria to release more calcium. In addition, production of adenosine triphosphate (ATP) may be stopped, and ATP synthase may in fact begin hydrolysing ATP instead of producing it (Stavrovskaya et al., Free Radical Biology and Medicine. Volume 38, Issue 6, pages 687-697).

Inadequate ATP production resulting from brain trauma can eliminate electrochemical gradients of certain ions. Glutamate transporters require the maintenance of these ion gradients in order to remove glutamate from the extracellular space. The loss of ion gradients results not only in the halting of glutamate uptake, but also in the reversal of the transporters, causing them to release glutamate and aspartate into the extracellular space. This results in a buildup of glutamate and further damaging activation of glutamate receptors (Siegel et al., Basic Neurochemistry: Molecular, Cellular, and Medical Aspects, 6th ed., Lippincott, Williams & Wilkins, Philadelphia, 1999).

At the molecular level, calcium influx is not the only event responsible for apoptosis induced by excitoxicity. Recently it has been noted that extrasynaptic NMDA receptor activation, triggered by glutamate exposure or hypoxic/ischemic conditions, activates a CREB (cAMP response element binding protein) shut-off, which in turn, causes loss of mitochondrial membrane potential and apoptosis (Hardingham et al., Nat Neurosci 5(5):405-414, 2002). On the other hand, activation of synaptic NMDA receptors only activates the CREB pathway which activates BDNF (brain-derived neurotrophic factor), not apoptosis.

Glutamate antagonists have been known to stop neurotoxicity due to excitotoxins. Methods for treating neurological injuries and neurodegenerative diseases have largely focused on finding more potent glutamate antagonists. However, this approach has not been very effective in clinical settings.

For example, the blood-clot dissolver tissue plasminogen activator (TPA) can reduce the disability of people who survive an ischemic stroke and has been an important breakthrough in the treatment of acute neurological disorders. However, there is only a 3-hour window within which a patient must receive the TPA treatment from the time of the ischemic insult in order for the treatment to be effective. Today, more than 40% of stroke patients do not reach medical personnel within this critical time period. Furthermore, patients with hemorrhage must be excluded from TPA treatments. In view of these statistics, methods for widening this critical treatment window for neuroprotective treatments have been an area of intensive research. And because neural damage results not only from hypoxic cell death, but also from excitotoxic cell death, these methods have aimed at inhibiting glutamate release or calpain activity.

Recently, calpain inhibitors have been found to be neuroprotective in animal models of stroke (Bartus et al., Stroke 25(11):2265-2270, 1994; Goll et al., Physiol Rev 83(3):731-801, 2003; Liebetrau et al., Neurol Res 27(5):466-470, 2005; Markgraf et al., Stroke 29(1):152-158, 1998; Wu and Lynch, Mol Neurobiol 33(3):215-236, 2006); however, no calpain inhibitor has reached the clinic. This is likely due to the relatively low specificity of existing calpain inhibitors as well as to the broad spectrum of calpain substrates and functions in which this family of enzymes is implicated. Thus, there still exits a need for more efficient pharmacological treatments that have reduced side effects.

SUMMARY OF THE INVENTION

This invention relates to compositions and methods for diagnosis and treatment of neurological injuries and neurodegenerative disorders.

In one aspect, the invention features a composition comprising a peptide or a peptidomimetic thereof that inhibits the C-terminal domain truncation of mGluR1α by calpain. The peptide is 10-30, 15-20, or 14 amino acids in length and contains a sequence that is at least 70%, 80%, 90%, or 95% homologous to VIKPLTKSYQGSGK (SEQ ID NO: 1). Preferably, the peptide contains or consists of VIKPLTKSYQGSGK (SEQ ID NO: 1). In particular, the composition may contain VIKPLTKGGQGSGK (SEQ ID NO: 2), VIKPLTK-dS-dY-QGSGK .(SEQ ID NO: 3), VIKPLTK-dA-dF-QGSGK (SEQ ID NO: 4), YGRKKRRQRRRVIKPLTKSYQGSGK (SEQ ID NO: 5), RRRQRRKKRGYVIKPLTKSYQGSGK (SEQ ID NO: 6), VIKPLTKSYQGSGKYGRKKRRQRRR (SEQ ID NO: 7), or

(SEQ ID NO: 8)

In some embodiments, the peptidominetic is PNA; in some embodiments, the composition further comprises a pharmaceutically acceptable carrier.

In another aspect, the invention features a method of detecting the C-terminal domain truncation of mGluR1α by calpain. The method comprises providing a sample containing mGluR1α and calpain and determining the presence or absence of the C-terminal domain truncation of mGluR1α by the calpain. In some embodiments, the sample contains a neuron; in some embodiments, the sample is a neural tissue sample from a subject.

A method of inhibiting the C-terminal domain truncation of mGluR1α by calpain is also provided. In one embodiment, the method comprises contacting calpain with a composition of the invention, thereby inhibiting the C-terminal domain truncation of mGluR1α by the calpain. In another embodiment, the method comprises detecting the presence of the C-terminal domain truncation of mGluR1α in a neuron and contacting the neuron with an agent that inhibits the C-terminal domain truncation of mGluR1α.

The C-terminal domain truncation of mGluR1α may be determined by identifying the N-terminal fragment of mGluR1α or the C-terminal fragment of mGluR1α, or by identifying the N-terminal fragment of mGluR1α in the axon of a neuron.

An agent that inhibits the C-terminal domain truncation of mGluR1α may be a composition of the invention, APV, an antagonist of NMDAR containing subunit NR2B such as ifenprodil, or calpain inhibitor III.

Further within the invention is a method of identifying a compound that inhibits the C-terminal domain truncation of mGluR1α, and preferably, does not inhibit calpain-mediated spectrin truncation.

In one embodiment, the method comprises providing a system containing calpain and mGluR1α, contacting the system with a test compound, and detecting the C-terminal domain truncation of mGluR1α in the system. If the C-terminal domain truncation of mGluR1α in the system is less than the C-terminal domain truncation of mGluR1α in a control system that is not contacted with the test compound, the test compound is identified as a candidate for inhibiting the C-terminal domain truncation of mGluR1α. The system may further contain a brain membrane and calcium.

In another embodiment, the method comprises providing a neuron, contacting the neuron with a test compound, and detecting the C-terminal domain truncation of mGluR1α in the neuron. If the C-terminal domain truncation of mGluR1α in the neuron is less than the C-terminal domain truncation of mGluR1α in a control neuron that is not contacted with the test compound, the test compound is identified as a candidate for inhibiting the C-terminal domain truncation of mGluR1α.

The above-mentioned and other features of this invention and the manner of obtaining and using them will become more apparent, and will be best understood, by reference to the following description, taken in conjunction with the accompanying drawings. These drawings depict only typical embodiments of the invention and do not therefore limit its scope.

DETAILED DESCRIPTION OF THE INVENTION

Figure 1:
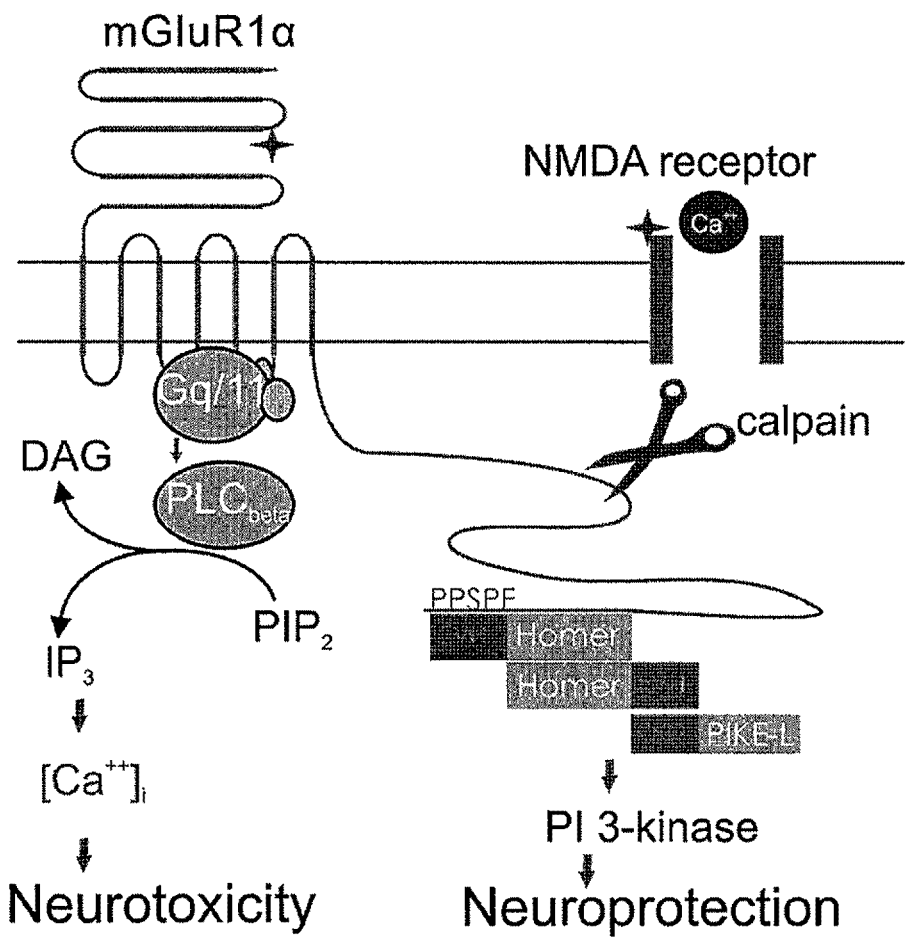
FIG. 1 shows a diagram illustrating the glutamate receptor mediated excitotoxicity mechanism.

As noted above, most attempts at treating neurological injuries and neurodegenerative diseases have thus far been unsatisfactory. One reason for the difficulty is that most NMDA receptors antagonists or calpain inhibitors can not efficiently cross the blood-brain barrier to reach the intended targets. Even if an inhibitor/antagonist can cross the blood-brain barrier, direct inhibition of NMDA receptors or calpain almost invariably causes many side effects because these targets may be involved in many other metabolic/regulatory pathways other than excitotoxicity. By blocking these targets, other normal cellular functions may be undesirably affected.

The present invention is based at least in part upon the unexpected discovery that activation of NMDAR induces calpain-mediated truncation of mGluR1α at Ser936 of its C-terminus. The truncation, in turn, disrupts the neuroprotective mGluR1-PI3K-Akt signaling but keeps the neurotoxic PLC-$Ca^{++}$ releasing pathway functional. The neurotoxic PLC-$Ca^{++}$ pathway further incurs neural damage, which, in turn further elevates glutamate level to further stimulate NMDA receptors, thereby, forming a positive feedback loop in NMDAR-mediated excitotoxicity. This discovery has many utilities, including, but not limited to pharmacological intervention of neurological damage by excitotoxicity via blockade of mGluR1α C-terminal truncation by calpain, research tool for metabolic and biochemical studies, and screening assays for identification of novel pharmacological agents.

Accordingly, the invention provides a composition comprising a compound that inhibits the C-terminal domain truncation of mGluR1α by calpain. The compound may be a peptide, a peptidomimetic, or a small organic molecule.

A peptide of the invention may range from about 10 to about 30 amino acids in length, preferably from about 15 to about 20 amino acids in length, and more preferably be about 14 amino acids in length.

The peptide may comprise a sequence having a substantial sequence homology to VIKPLTKSYQGSGK (SEQ ID NO: 1), wherein the sequence homology is preferably in the range of from more than 70% to more than 90%, more preferably from more than 80% to more than 95%.

In some embodiments, the peptide is a variant of VIKPLTKSYQGSGK (SEQ ID NO: 1). For example, the calpain cleavage site (i.e., SY in VIKPLTKSYQGSGK (SEQ ID NO: 1)) may be replaced with glycines (i.e., VIKPLTK GGQGSGK (SEQ ID NO: 2)), their d-form counterparts (i.e., VIKPLTK-dS-dY-QGSGK (SEQ ID NO: 3)), or d-alanine and d-phenylalanine (i.e., VIKPLTK-dA-dF-QGSGK (SEQ ID NO: 4)).

The peptide may be manufactured by direct chemical synthesis, expressed in a cellular expression system, or by any other peptide production means commonly known in the art.

A "peptidomimetic," as used herein, is a small protein-like chain designed to mimic a peptide. They typically arise from modification of an existing peptide in order to alter the molecule's properties. For example, they may arise from modifications to change the molecule's stability or biological activity. These modifications may involve changes to the peptide that will not occur naturally (such as altered backbones and the incorporation of nonnatural amino acids).

An exemplary peptidominetic is PNA, which may have the advantage of being non-digestible by proteases. Other candidates for peptidomimetics may include peptide analogs that contain one or more amide bond replacements, a conformationally restricted amino acid unit, or other conformational constraint. Novel scaffolds designs to replace the entire backbone while retaining isosteric topology are also contemplated.

Numerous methods have been described in the literature for methods and approaches for generating peptidomimetics. A person of ordinary skill in the art can readily find the appropriate guidance to implement the foregoing peptidomimetics. Goodman et al. and Bursavich et al. have published excellent recent overview of peptidomimetics (Goodman et al., Peptidomimetic building blocks for drug discovery: An overview, Pure & Appl. Chem., Vol. 68, No. 6, pp. 1303-1308, 1996; Bursavich et al., Designing Non-Peptide Peptidomimetics in the 21st Century: Inhibitors Targeting Conformational Ensembles, J Med Chem 45(3):541-558, 2002).

A compound of the invention may be delivered to a desired location by a delivery system. The delivery system is preferably biocompatible, easy to manufacture, and safe. Exemplary delivery systems include, but are not limited to, a fusion peptide, a fusion protein, an antibody conjugate, an engineered virus, nanoparticles, and liposomes. Various delivery systems have been recently described to transport small peptides across cell membranes and through the blood-brain barrier (see, e.g., Pardridge, Molecular Trojan horses for blood-brain barrier drug delivery. Curr Opin Pharmacol 6(5): 494-500, 2006).

For example, when the compound is a peptide, the delivery system may preferably be a fusion peptide comprising a tat fragment having YGRKKRRQRRR (SEQ ID NO: 9) and the peptide. The tat sequence may be fused to the peptide in both Y to R direction or R to Y direction. That is, the fusion peptide may be YGRKKRRQRRRVIKPLTKSYQGSGK (SEQ ID NO: 5), RRRQRRKKRGYVIKPLTKSYQGSGK (SEQ ID NO: 6), or VIKPLTKSYQGSGKYGRKKRRQRRR (SEQ ID NO: 7). In addition, the tat sequence and the peptide may be linked with an S—S bond between two cysteine residues added in the N-terminal position of the tat sequence and the peptide:

(SEQ ID NO: 8)

Once inside the cell, the S—S bond is reduced and the peptide is released, resulting in enhanced potency of the peptide.

The compounds of the invention can be incorporated into pharmaceutical compositions. Such compositions typically include the compounds and pharmaceutically acceptable carriers. "Pharmaceutically acceptable carriers" include solvents, dispersion media, coatings, antibacterial and antifungal agents, isotonic and absorption delaying agents, and the like, compatible with pharmaceutical administration.

A pharmaceutical composition is formulated to be compatible with its intended route of administration. See, e.g., U.S. Pat. No. 6,756,196. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

The compositions of the invention may be prepared with carriers that will protect the compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. "Dosage unit form," as used herein, refers to physically discrete units suited as unitary dosages for the subject to be treated, each unit containing a predetermined quantity of an active compound calculated to produce the desired therapeutic effect in association with the required pharmaceutical carrier.

The dosage required for treating a subject depends on the choice of the route of administration, the nature of the formulation, the nature of the subject's illness, the subject's size, weight, surface area, age, and sex, other drugs being administered, and the judgment of the attending physician. Suitable dosages are in the range of 0.01-100.0 mg/kg. Wide variations in the needed dosage are to be expected in view of the variety of compounds available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

The invention also provides a method of detecting the C-terminal domain truncation of mGluR1α by calpain. mGluR1α sequences are known in the art. See, for example, GenBank accession No. Q13255 for the human mGluR1α sequence, GenBank accession No. P97772 for the mouse mGluR1α sequence, and GenBank accession No. P23385 for the rat mGluR1α sequence. The "C-terminal domain" of mGluR1α refers to the portion of mGluR1α located to the C-terminal of the calpain cleavage site. For example, calpain cleaves rat mGluR1α between S936 and Y937. The C-terminal domain of rat mGluR1α starts with Y937 and extends to the C-terminal of the protein.

To detect the C-terminal domain truncation of mGluR1α by calpain, a sample containing mGluR1α and calpain is provided. The sample may be a mixture of mGluR1α and calpain; alternatively, the sample may contain a cultured neuron, or may be a neural tissue sample from a subject. The presence or absence of the C-terminal domain truncation of mGluR1α by the calpain is then determined using various techniques known in the art. One method is to detect the presence of the N-terminal or C-terminal fragment of mGluR1α generated by calpain cleavage. The "N-terminal fragment of mGluR1α" refers to the fragment of mGluR1α containing the amino acid sequence to the N-terminal of the calpain cleavage site, whereas the "C-terminal fragment of mGluR1α" refers to the fragment of mGluR1α containing the amino acid sequence to the C-terminal of the calpain cleavage site.

Antibodies (monoclonal or polyclonal) that bind specifically to the N-terminal or C-terminal fragment of mGluR1α may be employed in detecting the target proteins. In such assays, an antibody itself or a secondary antibody that binds to it can be detectably labeled. Alternatively, the antibody can be conjugated with biotin, and detectably labeled avidin can be used to detect the presence of the biotinylated antibody. Combinations of these approaches (including "multi-layer sandwich" assays) familiar to those in the art can be used to enhance the sensitivity of the methodologies. Some of these protein-detecting assays (e.g., ELISA or Western blot) can be applied to lysates of test cells, and others (e.g., immunohistological methods or fluorescence flow cytometry) applied to unlysed tissues or cell suspensions. Methods of detecting a label depend on the nature of the label and are known in the art. Appropriate labels include, without limitation, radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include immunoprecipitation or complement fixation assays. The presence of the N-terminal or C-terminal fragment of mGluR1α may also be detected with Gas Chromatography/Mass Spectrometry (GCMS) based on the specific molecular weight, or by isoelectric filtration techniques. In addition, localization of the N-terminal fragment of mGluR1α in the axon of a neuron indicates the presence of the C-terminal domain truncation of mGluR1α by the calpain.

Since the C-terminal domain truncation of mGluR1α by calpain disrupts the neuroprotective mGluR1-PI3K-Akt signaling and results in a positive feedback that amplifies the excitotoxicity cascade mediated by the PLC-$Ca^{++}$ pathway, the presence of the C-terminal domain truncation of mGluR1α by calpain is indicative of neurological injuries or neurodegenerative disorders. Therefore, this method may be used for diagnosis of neurological injuries or neurodegenerative disorders, including but not limited to Parkinson's disease, Huntington's disease, traumatic brain injury, and stroke.

The invention additionally provides a method of inhibiting the C-terminal domain truncation of mGluR1α by calpain in vitro or in vivo. One method of the invention comprises contacting calpain with a composition of the invention, thereby inhibiting the C-terminal domain truncation of mGluR1α by the calpain. Another method of the invention comprises detecting the presence of the C-terminal domain truncation of mGluR1α in a neuron according to the method described above, and contacting the neuron with an agent that inhibits the C-terminal domain truncation of mGluR1α. The agent may be a composition of the invention, APV, an antagonist of NMDAR containing subunit NR2B such as ifenprodil, or calpain inhibitor III. In some embodiments, the agent is used in combination with a subthreshold concentration (i.e., a concentration which by itself does not produce a pharmacological effect) of a calpain inhibitor to increase the potency for neuroprotection.

This method is useful for treating a subject suffering from a neurological injury and neurodegenerative disorder. As used herein, a "subject" refers to a human or animal, including all mammals such as primates (particularly higher primates), sheep, dog, rodents (e.g., mouse or rat), guinea pig, goat, pig, cat, rabbit, and cow. In a preferred embodiment, the subject is a human. In another embodiment, the subject is an experimental animal or animal suitable as a disease model.

To treat a subject suffering from a neurological injury and neurodegenerative disorder, an effective amount of an agent is administered to the subject to inhibit the C-terminal domain truncation of mGluR1α in the subject. A subject to be treated may be identified in the judgment of the subject or a health care professional, and can be subjective (e.g., opinion) or objective (e.g., measurable by a test or diagnostic method such as those described above).

A "treatment" is defined as administration of a substance to a subject with the purpose to cure, alleviate, relieve, remedy, prevent, or ameliorate an injury or disorder, symptoms of the injury or disorder, a disease state secondary to the injury or disorder, or predisposition toward the injury or disorder.

An "effective amount" is an amount of a compound that is capable of producing a medically desirable result in a treated subject. The medically desirable result may be objective (i.e., measurable by some test or marker) or subjective (i.e., subject gives an indication of or feels an effect).

In the case of stroke or traumatic brain injury, the agent is preferably administered in a single intravenous injection. For more slowly developing neurodegenerative diseases, the agent is preferably in repeated administration by the best appropriate route of administration.

The discovery of the C-terminal domain truncation of mGluR1α by calpain in connection with excitotoxicity is useful for identifying, e.g., in a high-throughput format, compounds for inhibiting the C-terminal domain truncation of mGluR1α and for treating neurological injuries and neurodegenerative disorders. For example, a system containing calpain and mGluR1α may be provided and contacted with a test compound. The C-terminal domain truncation of mGluR1α in the system is then determined. If the C-terminal domain truncation of mGluR1α in the system is less than the C-terminal domain truncation of mGluR1α in a control system that is not contacted with the test compound, the test compound is identified as a candidate for inhibiting the C-terminal domain truncation of mGluR1α and for treating neurological injuries and neurodegenerative disorders. In some embodiments, the system may further contain a brain membrane and calcium. A "brain membrane" may be obtained by homogenizing a brain tissue and subject the homogenized tissue to centrifugation over a sucrose-gradient. The homogenized tissue can be separated into different fractions according to their density. One of the fractions is mainly composed of cell membranes and is called "brain membrane" fraction.

Similarly, a cultured neuron or a subject (e.g., a subject suffering from a neurological injury or neurodegenerative disorder) may be contacted with a test compound. Samples of neural tissues may be obtained from the subject. The C-terminal domain truncation of mGluR1α in the neuron or the neural tissue sample is then determined. If the C-terminal domain truncation of mGluR1α in the neuron or the neural tissue sample is less than the C-terminal domain truncation of mGluR1α in a respective control neuron or neural tissue sample that is not contacted with the test compound, the test compound is identified as a candidate for inhibiting the C-terminal domain truncation of mGluR1α and for treating neurological injuries and neurodegenerative disorders.

The test compounds of the present invention can be obtained using any of the numerous approaches (e.g., combinatorial library methods) known in the art. See, e.g., U.S. Pat. No. 6,462,187. Such libraries include, without limitation, peptide libraries, peptoid libraries (libraries of molecules having the functionalities of peptides, but with a novel, non-peptide backbone that is resistant to enzymatic degradation), spatially addressable parallel solid phase or solution phase libraries, synthetic libraries obtained by deconvolution or affinity chromatography selection, and the "one-bead one-compound" libraries. Compounds in the last three libraries can be peptides, non-peptide oligomers, or small molecules. Examples of methods for synthesizing molecular libraries can be found in the art. Libraries of compounds may be presented in solution, or on beads, chips, bacteria, spores, plasmids, or phages.

The candidate compounds so identified can be used to inhibit the C-terminal domain truncation of mGluR1α by calpain in vitro and in vivo and to treat neurological injuries and neurodegenerative disorders. To reduce side effects, the candidate compounds preferably do not inhibit calpain-mediated spectrin truncation.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

The mGluR1α Excitotoxicity Positive Feedback Loop

Glutamate is the major excitatory neurotransmitter in the brain.

Receptors for glutamate consist of three types of ionotropic glutamate receptors, namely NMDA, AMPA and kainate receptors, and three groups of metabotropic glutamate receptors. In addition to their physiological roles in normal neurotransmission, glutamate receptors play critical roles in neuronal death resulting from ischemia and other neurodegenerative diseases. Ionotropic glutamate receptors, especially NMDA receptors, have been repeatedly shown to contribute to excitotoxicity. However, the roles of metabotropic glutamate receptors, especially of group I mGluRs (mGluR1 and mGluR5) in excitotoxicity have been hotly debated.

Activation of group I mGluRs appears to be neuroprotective under various conditions. The agonist of group I mGluRs, DHPG, prevented and reversed NO-induced neurotoxicity in primary cultures of hippocampal neurons and the neurotoxic effect of hydrogen peroxide or platelet-activating factor in cortical neuronal cultures. Activation of mGluRs also protected neurons from oxidative stress. In organotypic hippocampal slice cultures, activation of mGluR1 before exposure to NMDA protected against NMDA-induced excitotoxicity. Furthermore, selective blockade of mGluRI was shown to exacerbate Aβ toxicity. Recent studies indicated that the neuroprotective effects of mGluRI were mediated through the formation and activation of the mGluRI-Homer-PIKE-L signaling complex (PIKE-L is the longer isoform of phosphoinositide 3 kinase enhancer). Activation of PI3K and Akt by mGluRI was also reported in another independent study.

However, in cerebral ischemia, numerous experiments have demonstrated neurotoxic effects of mGluRI activation. For example, in both in vivo and in vitro models of cerebral ischemia, activation of mGluRI, especially of mGluR1, is neurotoxic while antagonists of mGluR1 are neuroprotective. Through diligent experimentations, the inventors have discovered interactions between NMDA receptor activation and mGluR1α that reconciles the conflicting observations. FIG. 1 depicts a schematic representation of this interaction. The experimental results are described in the following EXPERIMENTS section. The positive feedback loop of the NMDA receptor and mGluR1α is described in details below.

Referring to FIG. 1, the mGluR1α mediated signaling pathway is shown on the left-hand side of the figure. On the right-hand side of the figure is an NMDA-receptor and a calcium ion channel gated by the receptor. The 7-transmembrane G-protein coupled receptor (GPCR) mGluR1α is shown here in line figure, having its N-terminus on the extracellular side of the membrane and its C-terminus on the cytosolic side of the membrane. The mGluR1α mediates two signaling pathways: one mediated by the coupled G-protein portion Gq/11, herein referred to as the PLC-Ca$^{++}$ releasing pathway, leading to neurotoxicity, and one mediated by the C-terminal domain, herein referred to as the mGluR1-PI3K-Akt signaling pathway, leading to neuroprotection.

In this figure, when NMDA is activated by glutamate, it triggers an influx of Ca$^{++}$ ions through the ion channel, which, in turn, activates calpain (shown as the pair of scissors in the figure). The calpain then truncates the C-terminal domain of mGluR1α to deactivate the mGluR1-PI3K-Akt neuroprotective pathway, which results in enhanced neurotoxicity and increased glutamate release, thereby, forming a positive feedback loop.

EXPERIMENTS

1. Glutamate-Induced Truncation of mGluR1α C-Terminal Domain

Figure 2:
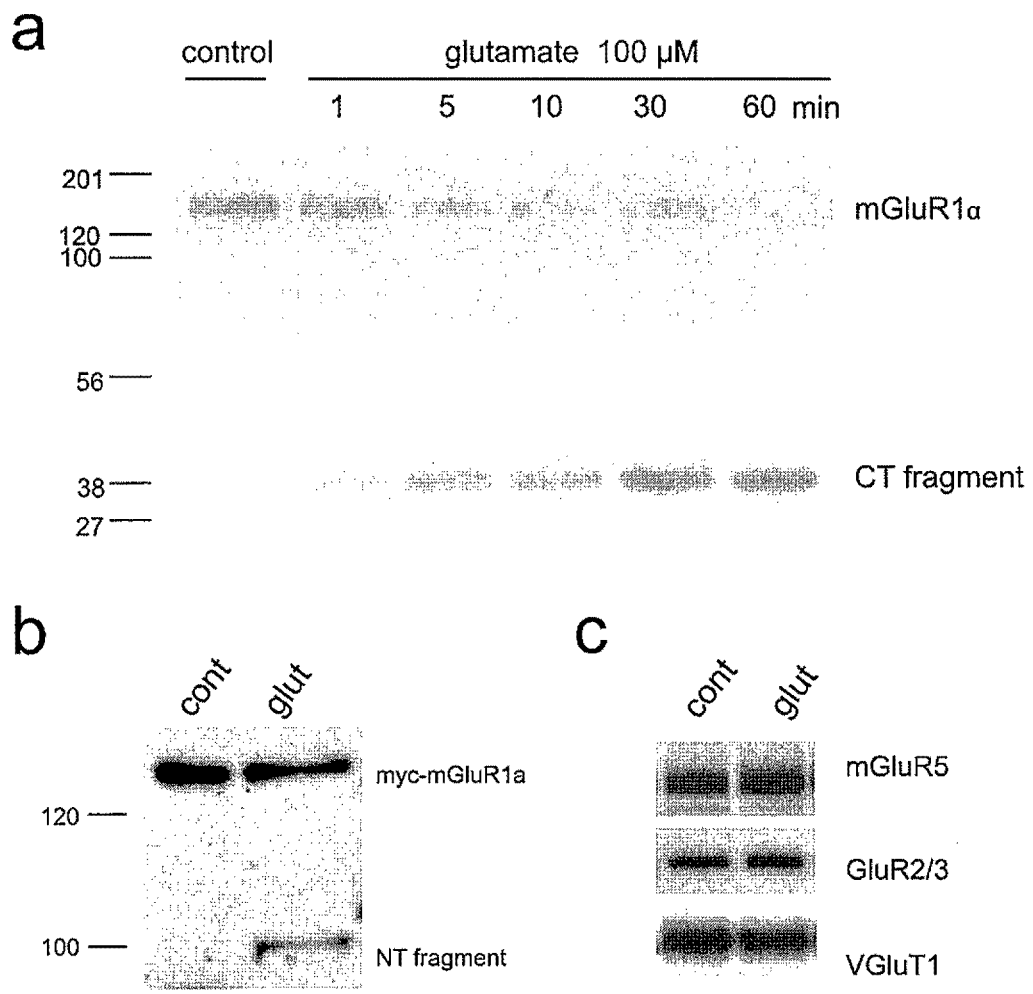
FIG. 2 shows the result of time-dependent glutamate excitotoxicity on cortical neurons.

FIG. 2 shows experimental data for glutamate induction of carboxyl-terminal truncation of mGluR1α. In FIG. 2A, cortical neurons were treated with 100 μM glutamate for the indicated times. Total cell lysates were separated by SDS-PAGE and probed with an antibody against the carboxyl terminus (residue 1142-1160) of mGluR1α. In FIG. 2B, cortical neurons were transfected with myc-mGluR1α (c-myc epitope located after Ala30 at the amino-terminus of mGluR1α) and treated with 100 μM glutamate for 60 min 1 week after transfection. Total cell lysates were probed with an anti-myc antibody. In FIG. 2C, cortical neurons were treated with 100 μM glutamate for 60 min. Total cell lysates were probed with antibodies against mGluR5, GluR2/3 and VGluT1 respectively.

To detect possible modifications of mGluR1α following glutamate-induced excitotoxicity, cultured cortical neurons (14-48 DIV) were incubated with 100 μM glutamate for different durations ranging from 1 to 60 minutes. Total cell lysate was collected immediately after treatment and subjected to SDS-PAGE and immunoblotting with an antibody against the carboxyl terminus (residues 1142-1160) of mGluR1α (FIG. 2A). Levels of the native mGluR1α band decreased with increasing incubation time, while the levels of a low-molecular weight band recognized by the antibody at about 38 kD increased, suggesting that truncation of mGluR1α occurred at the carboxyl terminus. The truncation was apparent at 1 min after glutamate treatment and by 60 min, staining of the native mGluR1α had almost completely disappeared (FIG. 2A). To probe the amino-terminus of mGluR1α after truncation, cortical neurons were transfected with an mGluR1α construct tagged with a myc epitope at the N-terminus (myc-mGluR1α, the EQKLISEEDL (SEQ ID NO: 10) epitope was inserted in frame after Ala30 of mGluR1α) after 3 days in vitro. Neurons were transfected with a calcium phosphate precipitation method modified for high transfection rate (Jian et al., Gene Ther 11:1301-1311, 2004). One week later, transfected neurons were treated with 100 μM glutamate for 1 hour and then collected and processed for Western blots. When probed with an anti-myc antibody, the blots revealed a low-molecular weight band at about 100 kD after glutamate treatment (FIG. 2B), which corresponds to the N-terminal fragment after truncation. The optical density of the original myc-mGluR1α did not decrease significantly, suggesting that only a small fraction of the overexpressed myc-mGluR1α was cleaved. Since the apparent molecular weight of mGluR1α on SDS-PAGE is about 140 kD, our data suggested that glutamate induced the truncation of mGluR1α in the carboxyl terminus, most likely at a single cleavage site.

To test for the specificity of glutamate-mediated truncation of mGluR1α, immunoblots were also probed with an antibody against mGluR5, another member of group I mGluRs, which shares a high similarity with mGluR1α. As shown in FIG. 2C, levels of mGluR5 were not significantly altered by glutamate treatment. Similarly, no significant changes occurred to the GluR2/3 subunits of AMPA receptors, or to the vesicular glutamate transporter (vGluT1), a presynaptic protein in glutamatergic synapses. Together, the data indicate that glutamate selectively induced the truncation of mGluR1 but not mGluR5 in cortical neurons.

2. Glutamate-Induced mGluR1α Truncation is Due to NMDA Receptor Activation

Figure 3:
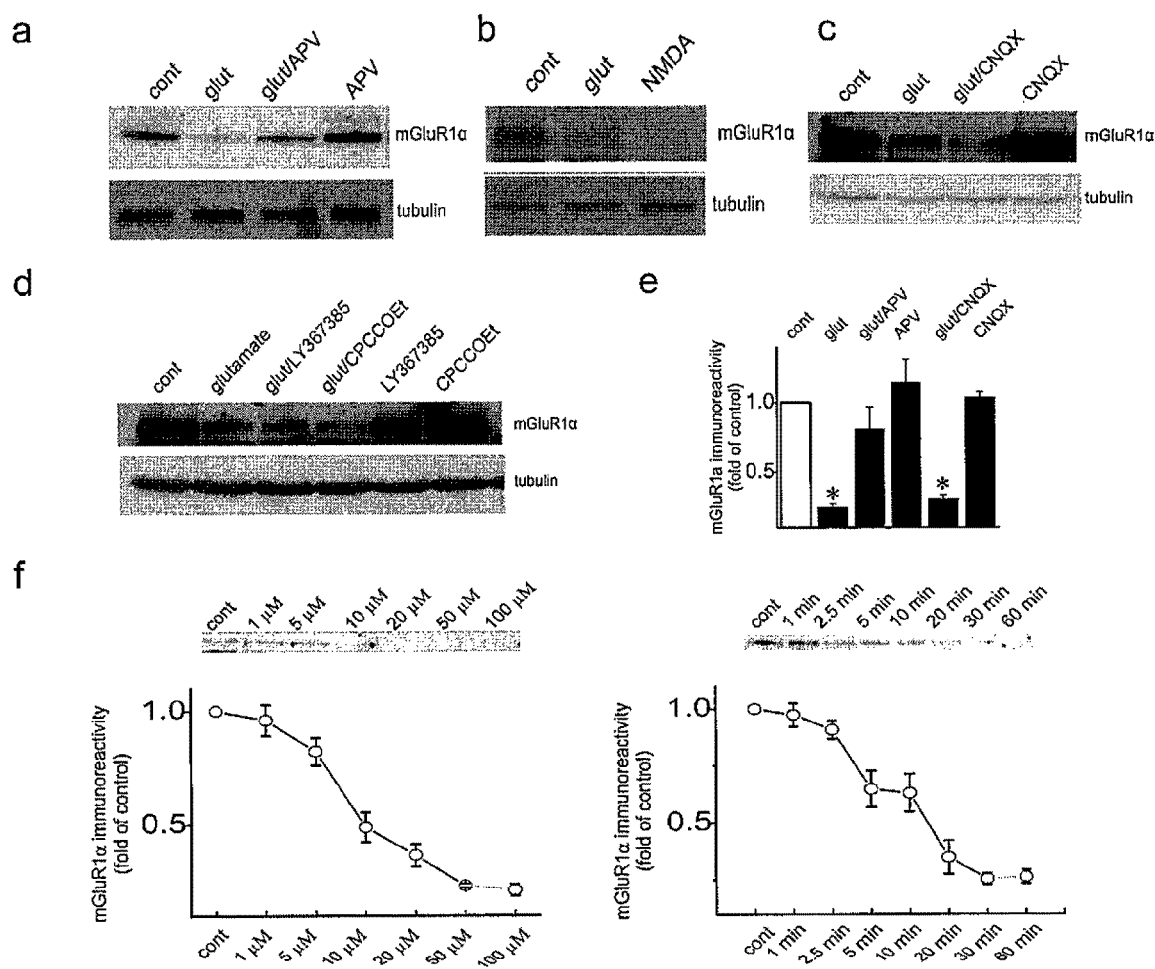
FIG. 3 shows the result of glutamate-induced mGluR1α truncation due to overactivation of NMDA receptors.

FIG. 3 shows data indicating that glutamate-induced mGluR1α truncation is due to overactivation of NMDA receptors. In FIGS. 3A, C and E, representative blots and bar graph indicate that glutamate (100 μM, 1-h)-induced truncation of mGluR1α is significantly blocked by the NMDA receptor antagonist APV, but not by the non-NMDA receptor antagonist CNQX. Staining with βIII-tubulin antibody served as loading control (* p<0.05). FIG. 3C shows a representative blot showing that NMDA treatment (100 μM, 1 h) produces a similar truncation of mGluR1α as glutamate (100 μM, 1 h). FIG. 3D shows a representative blot showing that the mGluR1 antagonists LY367385 (100 μM) and CPCCOEt (10 μM) do not block glutamate (100 μM, 1 h)-induced truncation of mGluR1α. FIGS. 3F and G show dose- and time-dependency of NMDA-induced mGluR1α-truncation. Cortical neurons were treated with NMDA at the indicated concentrations for 1 h or treated with NMDA (10 μM) for the indicated times. Total cell lysates were separated by SDS-PAGE and probed with antibodies against mGluR1α1142-1160, Results were normalized over control values and are means±s.e.m. of 4 experiments.

To identify which type(s) of glutamate receptor(s) was (were) involved in glutamate-induced truncation of mGluR1α, selective glutamate receptor antagonists were used. As shown in FIG. 3, a 1-hour treatment with 100 μM glutamate induced a significant reduction in the levels of mGluR1α (p<0.001; n=8, Student's t-test for Control vs. Glut). The competitive NMDA receptor antagonist APV (100 μM) completely blocked this effect (p<0.05, n=4, Student's t-test for Glut vs. Glut/APV; FIGS. 2A and E), whereas the non-NMDA glutamate receptor antagonist CNQX (100 μM, FIG. 2C) had no effect (p>0.05; n=4, Student's t-test for Glut vs. Glut/CNQX). To determine whether activation of mGluR1α itself was required for the truncation, two distinct mGluR1α antagonists were applied. As shown in FIG. 3D, neither the competitive mGluR1α antagonist LY367385 nor the non-competitive mGluR1α antagonist CPCCOEt blocked glutamate-induced truncation. The results indicate that only NMDA receptor activation is required for glutamate-induced mGluR1α truncation. For further confirmation, we verified that, when cortical cultures were incubated with NMDA (100 μM) for 1 hour, NMDA produced a degree of truncation of mGluR1α similar to glutamate (FIG. 3B). In summary, these data indicate that activation of NMDA receptors but not non-NMDA glutamate receptors results in truncation of the C-terminal domain of mGluR1α and that activation of mGluR1α itself is not required for this effect.

To further characterize NMDA-induced mGluR1α truncation, the concentration- and time-dependencies of the effects of NMDA were studied. Cortical neurons were first incubated with different concentrations of NMDA for a fixed period of time (1 hour) (FIG. 3F). The minimum concentration of NMDA required to induce a significant mGluR1α truncation was 10 μM (p<0.001, n=4, Student's t-test for Control vs. 10 μM), and the EC50 for NMDA was also about 10 μM. In a following experiment, cortical neurons were incubated with 10 μM NMDA for different durations ranging from 1 to 60 min (FIG. 3G). The minimum time required for 10 μM NMDA to induce truncation was 5 min (p<0.01, n=4, Student's t-test for Control vs. 5 min) and the truncation was maximal after 20 min treatment. Collectively, these results indicated that NMDA-induced mGluR1α truncation requires prolonged activation of NMDA receptors.

3. Calpain Truncates mGluR1α at Ser936

Figure 4:
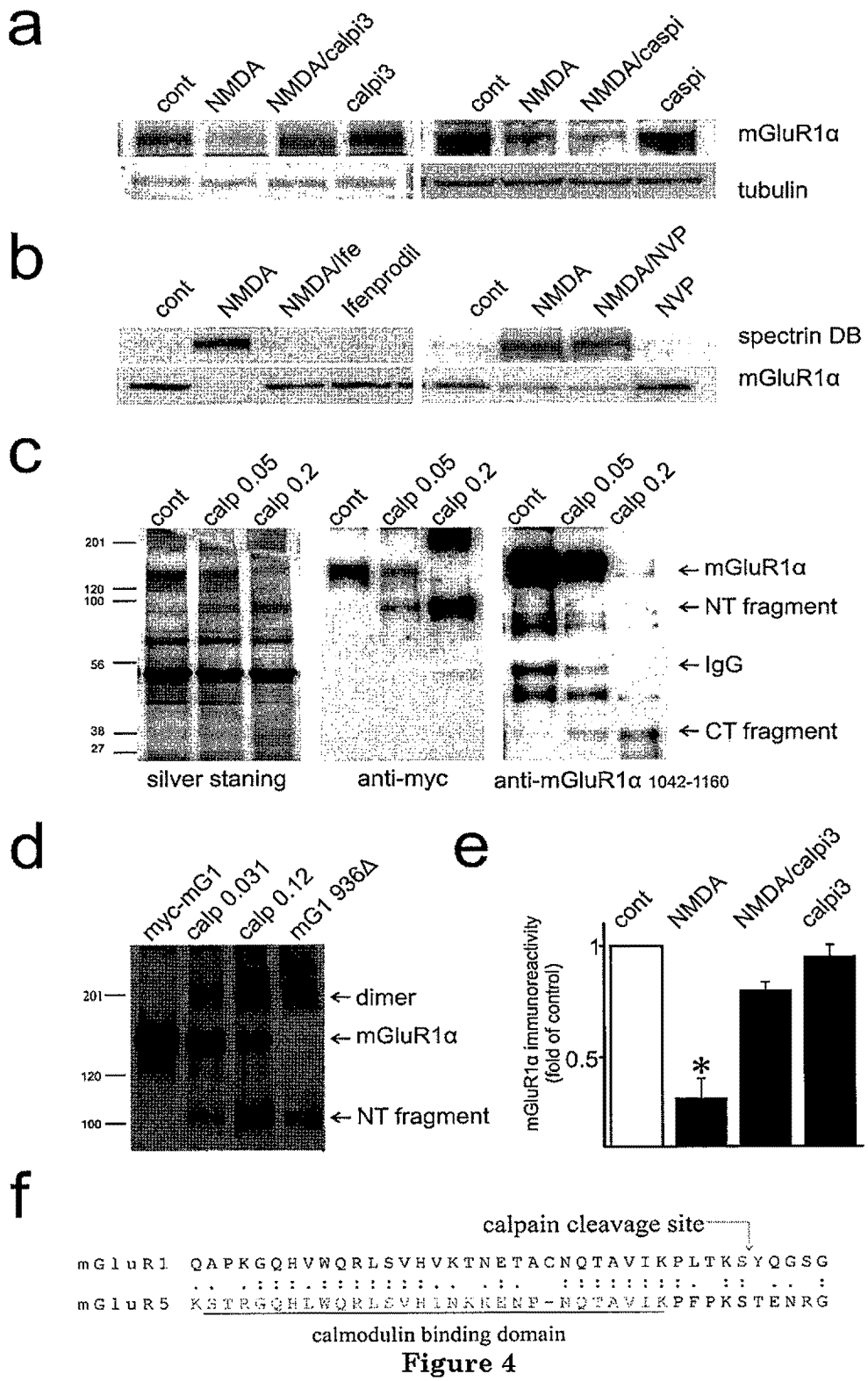
FIG. 4 shows the result of experiments identifying the cleavage site of the mGluR1α truncation by calpain.

FIG. 4 shows that mGluR1α is truncated by calpain at Ser936. In FIGS. 4A and E, representative blots and bar graph indicate that NMDA (100 μM, 1 h)-induced truncation of mGluR1α is significantly blocked by calpain inhibitor III (Calpi3, 10 μM; t=5.09, p<0.01; n=4, for NMDA vs. NMDA/Calpi3) but not by caspase inhibitor cpm-VAD-CHO (Caspi). FIG. 4B shows representative blots showing calpain activation by NMDA treatment. Cortical neurons were treated with NMDA (10 μM, 1 h). Total cell lysates were separated by SDS-PAGE and probed with antibodies against spectrin and mGluR1α$_{1142-1160}$, respectively. Only the degradation bands of spectrin (spectrin DB, at ~145 KD) are shown. NMDA-induced spectrin degradation and mGluR1α truncation were blocked by ifenprodil, a selective antagonist of NR2B subunit-containing NMDA receptors, but not NVP-AAM077, a selective antagonist for NR2A subunit-containing NMDA receptors. In FIG. 4C, purified myc-mGluR1α was digested with μ-calpain at the indicated concentrations (U/ml) for 30 min. The digested material was processed for SDS-PAGE and subjected to silver staining or immunoblots with anti-myc or anti-mGluR1α$_{1142-1160}$ antibodies. From silver staining, myc-mGluR1α (~140 kD) was cleaved by calpain into two bands of molecular weight of 100 kD (corresponding to the amino-terminal fragment, as it was immunostained by the anti-myc antibody) and 38 kD (corresponding to the carboxyl-terminal fragment, as it was immunostained by the anti-mGluR1α$_{1142-1160}$ antibody), respectively. FIG. 4D shows the result of immunoblots probed with an anti-myc antibody. The $1^{st}$ lane was the myc-mGluR1α immunoprecipitated from 293 cells; the $2^{nd}$ and $3^{rd}$ lanes were immunoprecipitated myc-mGluR1α digested with indicated concentration of calpain. The $4^{th}$ lane was the myc-mGluR1α936Δ immunoprecipiated from 293 cells and the band exhibited the same molecular weight as the amino-terminal fragment of digested myc-mGluR1α. FIG. 4F is the alignment of mGluR1 (902-941) and mGluR5 (889-927) surrounding the calpain cleavage site.

In this set of experiments, we determined which protease(s) mediated NMDA-induced truncation of mGluR1α. Previous studies have indicated that both the calcium-dependent neutral protease calpain and caspases could be activated by neurotoxic concentrations of NMDA. Cortical neurons were pretreated with a calpain inhibitor, the cell-permeable calpain-inhibitor III, or the caspase inhibitor cpm-VAD-CHO for 2 hours and then incubated in the absence or presence of 100 M NMDA for 1 hour. Pretreatment with calpain inhibitor III significantly blocked NMDA-induced truncation, while the cell permeable caspase inhibitor cpm-VAD-CHO had no effect (FIG. 4A). To further confirm calpain activation by NMDA under our experimental conditions, we determined the levels of the calpain-specific spectrin degradation fragments. The 145 kD spectrin degradation fragment (spectrin DB), which is widely used as a marker of calpain activation, could not be detected under control conditions (FIG. 4B); NMDA treatment resulted in a large increase in the levels of this degradation fragment. In addition, NMDA-mediated spectrin degradation could be blocked by ifenprodil (10 μM), a selective antagonist of NR2B subunit-containing NMDA receptors, but not NVP-AAM077 (0.4 μM), a selective antagonist for NR2A subunit-containing NMDA receptors. Similarly, NMDA-induced truncation of mGluR1α was selectively blocked by ifenprodil but not by NVP-AAM077 (FIG. 4B).

The involvement of calpain in mGluR1α truncation did not necessarily imply that calpain could directly cleave the C-terminus of mGluR1α. To test this possibility, we first transfected HEK293 cells with the N-terminus myc-epitope tagged mGluR1α. After 48 hours, transfected HEK cells were lysed and mGluR1α receptors were immunoprecipitated with an anti-mGluR1α C-terminus antibody and incubated with different concentrations of μ-calpain for 30 min. Aliquots of the precipitated proteins were processed for SDS-PAGE and silver staining, and the rest of the samples were used for Western blots with antibodies against anti-myc or anti-mGluR1α C-terminus, respectively. With silver staining, the density of the 145 kD band that represents the whole-length mGluR1α decreased dose-dependently with calpain treatment. In parallel, two additional bands appeared after calpain treatment with apparent molecular weights of 100 kD and 38 kD, respectively. The 100 kD band proved to be the N-terminus of mGluR1α derived from truncation since it reacted with the anti-myc antibody. Likewise, the 38 kD protein proved to be the C-terminus of mGluR1α as it was labeled with the anti-mGluR1α C-terminus antibody. These data indicated that calpain could directly cleave mGluR1α at the C-terminus.

From the size of the fragments of mGluR1α after cleavage, we deduced that the cleavage site of calpain in mGluR1α should be between residue I812 (the molecular weight of the sequence from Ile812 to the C-terminus is 38.25 kD) and Ser943 (the molecular weight from N-terminus to Ser943 is 105.62 kD). We therefore made a GST fusion construct with the sequence of mGluR1α from Ile812 to Ser943 attached to the C-terminus of GST. The GST fusion protein was expressed in and purified from BL21 *E. coli* and the purified protein was digested with calpain in the presence of 2 mM $CaCl_2$. The GST-mGluR1α fusion protein became about 2 kD smaller after digestion, suggesting that the cleavage site was close to Ser943. To obtain sufficient C-terminal fragments for Edman protein sequencing, another construct was made by fusing the mGluR1α sequence from Asn889 to Leu1058 to the C-terminus of GST. As expected, after digestion with calpain, this fusion protein generated a 10 kD fragment. The N-terminus of this fragment was sequenced to be YQGS with Edman degradation, indicating that the calpain cleavage site in mGluR1α is between Ser936 and Tyr937.

To obtain further confirmation of this truncation site, a stop codon was introduced into the myc-mGluR1α plasmid immediately after Ser936 to generate a construct for truncated mGluR1α (myc-mGluR1α936Δ). Following transfection in HEK293 cells, this construct generated a protein with the same apparent molecular weight (100 kD) as the mGluR1α N-terminal fragment generated after NMDA-induced truncation.

Based on this cutting sequence information, we had the following peptide synthesized: YGRKKRRQRRRVIKPLTKSYQGSGK (SEQ ID NO: 5) (tat-mGluR1 peptide). This sequence comprises the sequence of the HIV tat-peptide (YGRKKRRQRRR) (SEQ ID NO: 9), which has been widely used as a cargo for peptide or other molecules across cell membranes and the sequence surrounding the cutting site of the C-terminal domain of mGluR1α (VIKPLTKSYQGSGK, (SEQ ID NO: 1) note the SY cutting sequence).

4. C-Terminal Truncated mGluR1α Remains Functional

Figure 5:
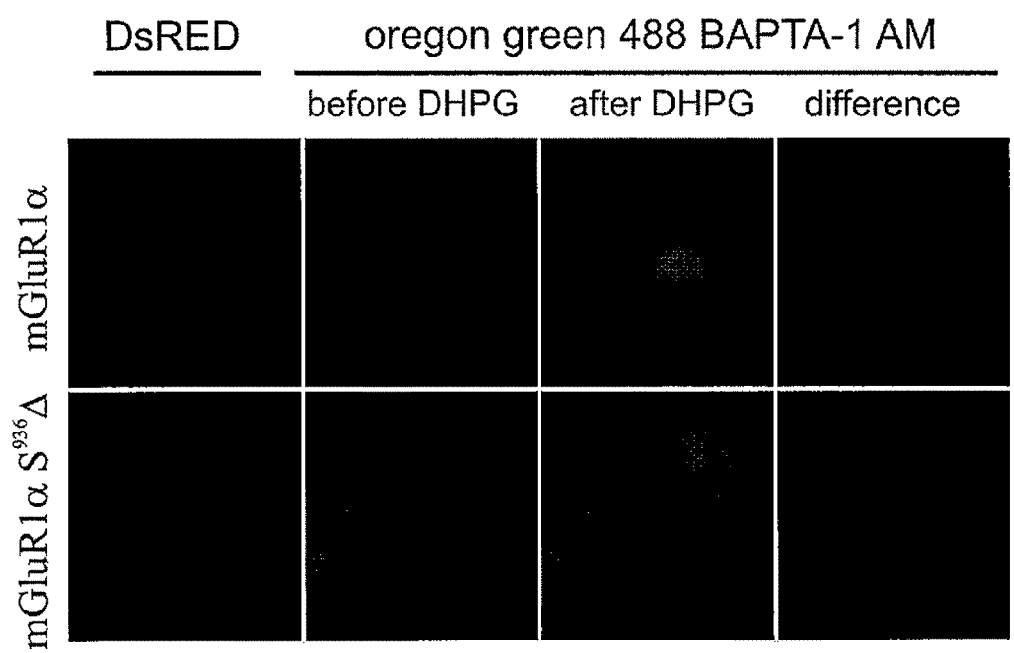
FIG. 5 shows that C-terminal truncated mGluR1α remains functional for increasing cytosolic free calcium.
Figure 5:
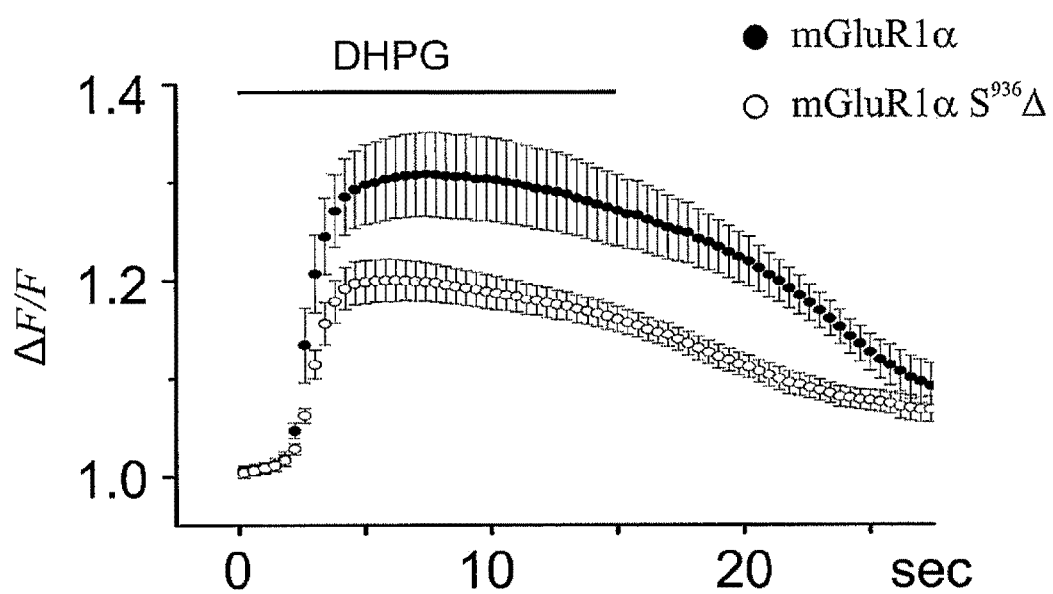

FIG. 5 shows that C-terminal truncated mGluR1α remains functional for increasing cytosolic free calcium. In this set of experiments, HEK293 cells were co-transfected with DsRed (red fluorescent protein) and wild-type myc-mGluR1α or truncated myc-mGluR1α936Δ. The mGluRI agonist DHPG was used to induce mGluR1α-mediated calcium transients. In FIG. 5A, photos in the left show the expression of DsRed, labeling transfected cells; photos in the middle illustrate the fluorescent signal from the calcium indicator Oregon green 488 BAPTA-1 AM before and after DHPG application; photos in the right are obtained by subtracting "before DHPG" from "after DHPG", thus representing DHPG-induced calcium transients. FIG. 5B shows quantification of DHPG-induced calcium transients in myc-mGluR1α or truncated myc-mGluR1α936Δ-transfected cells; results are means±S.E.M., n=8-10.

The main signaling mechanism activated by mGluR1α consists of PI hydrolysis through G-protein and phospholipase C, which eventually leads to calcium release from internal calcium stores. Therefore we first performed calcium imaging to determine whether mGluR1α remains functional following C-terminal truncation. Wild-type mGluR1 (myc-mGluR1α) or the truncated form (myc-mGluR1α936Δ) was cotransfected with DsRed into HEK293 cells. Forty-eight hours after transfection, cells were loaded with a calcium reporter, Oregon green 488 BAPTA-1 AM (0.63% in extracellular solution). As shown in FIG. 5, significant increase in intracellular calcium concentration could be detected after treatment of cells transfected with myc-mGluR1α with 100 μM DHPG, a selective agonist for group I mGluRs (max. ΔF/F=30.6±4.2%; n=8). This calcium response requires the activation of mGluR1α because no change in fluorescent signals could be observed in untransfected cells. In cells transfected with myc-mGluR1α936Δ, DHPG could induce qualitatively similar, although significantly smaller, calcium transients (max. ΔF/F=20.1 2.1%; n=10; $p<0.05$, Student's t-test for myc-mGluR1α vs. myc-mGluR1α936Δ). The data indicated that mGluR1α remains functional following C-terminal truncation at Ser936.

5. C-Terminal Truncation Alters mGluR1α Signaling

Figure 6:
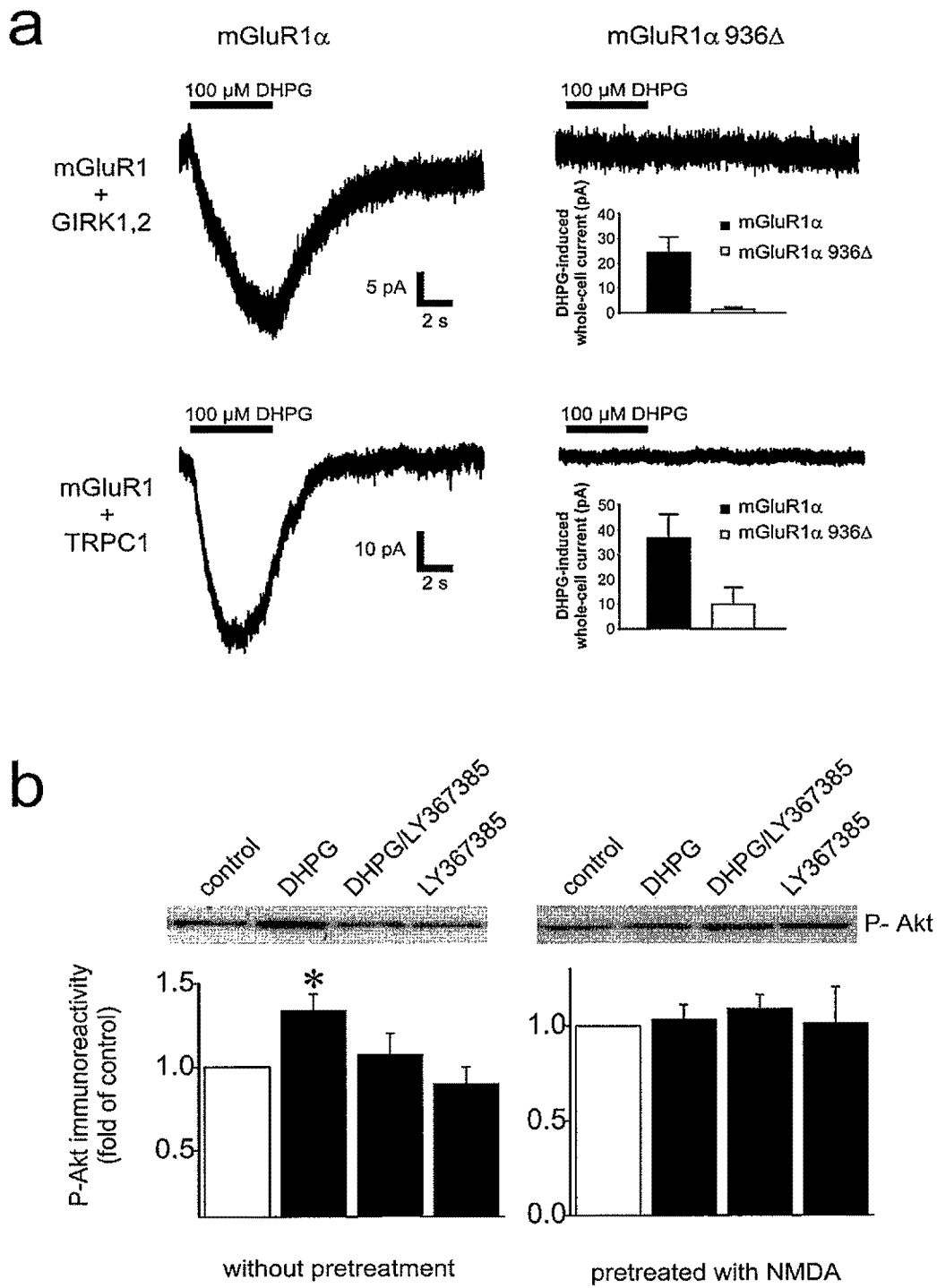
FIG. 6 shows that C-terminal truncation alters mGluR1α signaling.

FIG. 6 shows that C-terminal truncation alters mGluR1α signaling. FIG. 6A shows recordings of mGluR1-induced whole-cell currents in HEK293 cells. Representative current traces recorded from HEK293 cells transfected with either myc-mGluR1α (left panel) or myc-mGluR1α936Δ (right panel) and GIRK1, GIRK2 (top) or TRPC1 (bottom). DHPG (100 μM in extracellular solution) was applied using a fast perfusion system for the duration indicated by the scale bars. Each trace is the average of 5 continuous sweeps. The bar graphs represent the means±S.E.M. of DHPG-induced current amplitude recorded in cells transfected with myc-mGluR1α or myc-mGluR1α936Δplus GIRK1, GIRK2 (top right) or TRPC1 (bottom right) (n=3-7). In FIG. 6B, cortical neurons were pre-treated with NMDA (50 1μM, 1 h). Two hours after washing NMDA, neurons were treated with the mGluR1 agonist DHPG (50 μM) for 10 min in the absence or presence of LY367385. Total cell lysates were collected and probed with anti-Phospho Akt (Ser473) antibody. Without pretreatment with NMDA, DHPG increased the levels of Phospho-Akt (* $p<0.05$), an effect blocked by LY367385. After pre-treatment with NMDA, DHPG failed to increase Phospho-Akt levels.

Because activation of mGluR1α can also stimulate non-selective cation excitatory postsynaptic conductances (EP-SCs), we therefore analyzed mGluR1α-dependent currents before and after calpain-mediated truncation. We transfected HEK293 cells with either myc-mGluR1α or myc-mGluR1α936Δ plus GIRK1, GIRK2 or TRPC1. Application of DHPG evoked an inward current in HEK293 cells transfected with myc-mGluR1α and either TRPC1 or GIRK1,2 (FIG. 6A). The mean amplitude of DHPG-induced current in myc-mGluR1α/TRPC1-transfected cells was −36.7±9.6 pA (mean±s.e.m., n=7 cells), while in myc-mGluR1α/GIRK1,2-transfected cells, the average amplitude of the whole-cell current was −24.2±6.3 pA (n=5 cells). In contrast, whole-cell currents were markedly reduced or absent in cells transfected with myc-mGluR1α936Δ, with a mean amplitude of −9.7±6.8 pA in myc-mGluR1α936Δ/TRPC1-transfected cells (n=5) and −1.4±0.8 pA in myc-mGluR1α936Δ/GIRK1, 2-transfected cells (n=3). As illustrated in FIG. 6A, the whole-cell response induced by wild-type mGluR1 was significantly greater than that mediated by truncated mGluR1 (p<0.05, t-test for myc-mGluR1α vs. myc-mGluR1α936Δ in both TRPC1- and GIRK1,2-transfected cells).

As reported in previous studies, mGluR1 activation can stimulate the PI3K-Akt signaling pathway through the mGluRI-Homer-PIEL-PI3K signaling complex. Since the Homer-binding domain of mGluR1α is located in the extreme C-terminus, which is removed after calpain-mediated truncation, it was interesting to determine whether this signaling mechanism remained functional. We first induced mGluR1α truncation by treating cortical neurons with 50 μM NMDA for 1 hour. Two hours after washing out NMDA, neurons were incubated with the mGluRI agonist DHPG (50 μM) for 10 min. Neurons were then lysed and levels of phosphorylated Akt were determined on Western blots. Consistent with a previous study, in cortical neurons that were not pretreated with NMDA, DHPG induced an increase in phosphorylated Akt levels (p<0.05, n=4, Student's t-test for Control vs. DHPG), an effect which was blocked by the mGluR1 selective antagonist LY367385 (p<0.05, n=4, for DHPG+ LY367385 vs. DHPG) (FIG. 6B). After pre-treatment with NMDA, DHPG failed to increase Akt phosphorylation levels (p>0.05, n=4; Student's t-test for DHPG vs. Control in pretreated group). Thus, mGluR1α-PI3K-Akt signaling pathway was disrupted by calpain-mediated mGluR1α truncation.

6. C-Terminal Truncation Alters mGluR1α Targeting in Cortical Neurons

Figure 7:
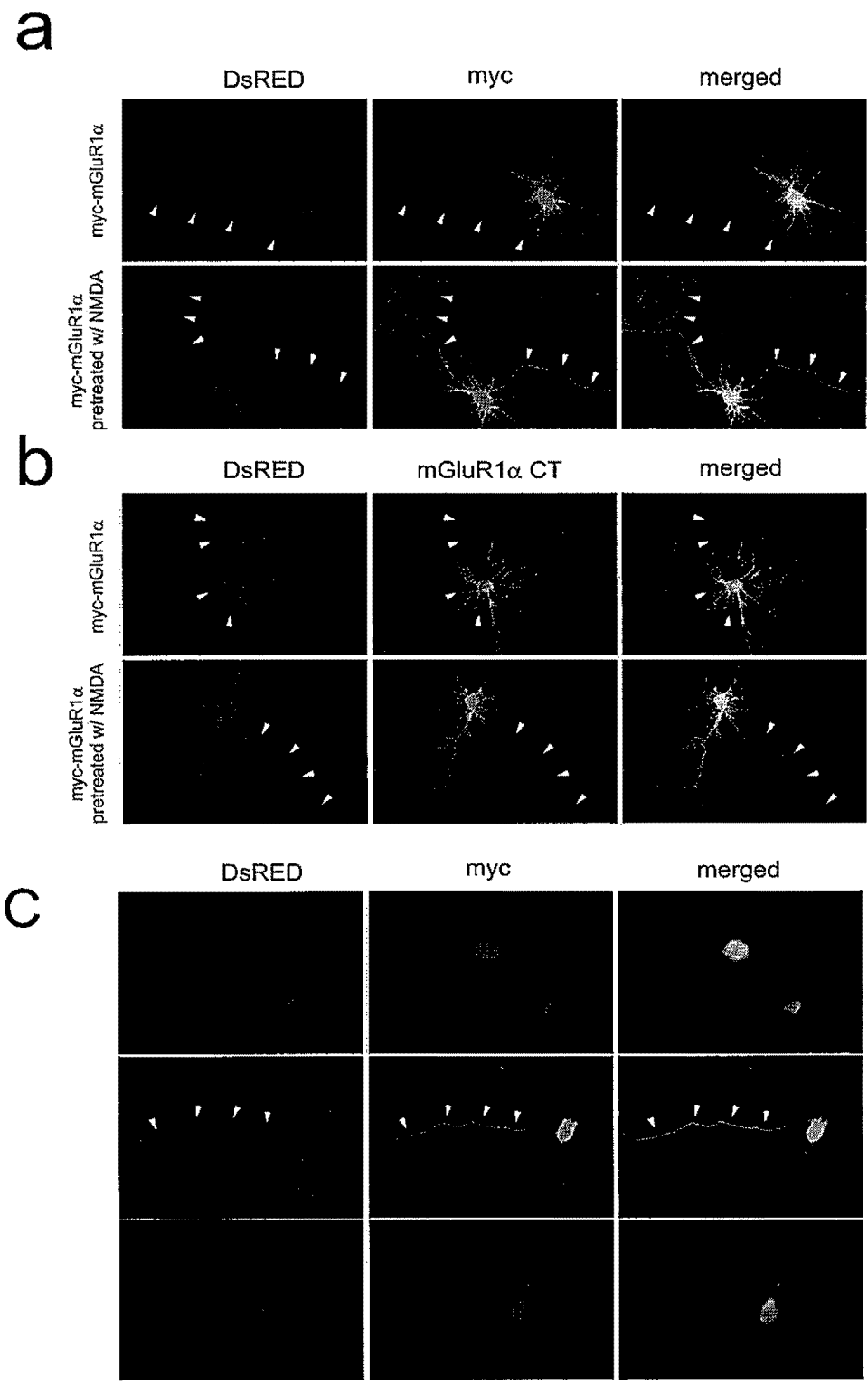
FIG. 7 shows that C-terminal truncation alters mGluR1α targeting.

FIG. 7 shows that C-terminal truncation alters mGluR1α targetting. In FIG. 7A, cortical neurons were co-transfected with DsRED and myc-mGluR1α. After 48 h, neurons were fixed and stained with anti-myc and anti-DsRED antibodies. Some of the neurons were pre-treated with NMDA (50 μM, 1 h), and recovered for 3 h after washing out NMDA before fixation. Myc-mGluR1α (upper panel) was absent in axons (arrowhead) under control conditions. After pre-treatment with NMDA (lower panel), staining of myc-mGluR1α appeared in the proximal segment of axons. In FIG. 7B, cortical neurons were co-transfected with DsRED and myc-mGluR1α. After 48 h, neurons were fixed and stained with anti-DsRED and anti-mGluR1α$_{1142-1160}$ antibodies with (lower panel) or without (upper panel) pretreatment with NMDA. Staining for mGluR1α was absent from axons in both conditions. In FIG. 7C, cortical neurons were co-transfected with DsRED and myc-mGluR1α936Δ. After 48 h, neurons were fixed and stained with anti-myc and anti-DsRED antibodies. In 73% of neurons, myc-immunoreactivity was restricted to cell bodies (upper panel, the arrowheads point to cell bodies); in 20% of neurons, myc-mGluR1α936Δ was preferentially targeted to axons (middle panel, the arrowheads point to axon). In 5% of neurons, myc-mGluR1α936Δ was preferentially targeted to dendrites and formed large clusters (lower panel, the arrowheads point to clusters in dendrites).

Despite the fact that mGluR1 is known to have some presynaptic effects in facilitating glutamate release, morphological studies have generally indicated a postsynaptic distribution of the receptors, mostly in the perisynaptic area. In cultured neurons, mGluR1α receptors also exhibit a dendrite-specific distribution. Previous studies have shown that the C-terminus domain of mGluR1α is crucial for its dendritic localization. Therefore, it was interesting to determine whether mGluR1α targeting was modified following calpain-mediated C-terminal truncation. Cortical neurons were transfected with myc-mGluR1α. After 48 hours, some neurons were treated with 50 μM NMDA for 1 hour and other neurons served as control. After 2 hours of washing out NMDA, neurons were fixed and stained with antibodies against the N-terminal myc-epitope or the C-terminus of mGluR1α respectively. As showed in FIG. 7A, wild-type mGluR1α was selectively targeted to dendrites and was almost completely excluded from axons. But in ~34% of neurons treated with NMDA (124 out of 367 neurons counted), the N-terminal fragment of wild-type mGluR1α could be detected in axons, especially in the proximal segment, whereas immunoreactivity against the C-terminus of mGluR1α was still restricted to dendrites (FIG. 7B). These results indicated that NMDA-induced C-terminal truncation altered mGluR1α targeting from postsynaptic to presynaptic sites.

To test whether NMDA-induced translocation of mGluR1α from dendrites to axons was an active process or a passive diffusion after truncation, we transfected cortical neurons with myc-mGluR1α936Δ and studied its targeting. 48 hours after transfection. The targeting of mGluR1α936Δ was dramatically different from that of wild-type mGluR1α. In the majority of transfected neurons (~73%, 500 out of 681 neurons counted), immunostaining for myc-tag was strictly restricted to cell bodies (FIG. 7C, upper panel). The cell-body restriction was the same when immunostaining was performed 6 days after transfection, suggesting that it was not the result of a delay in expression or delivery but was mediated by targeting signals. In a smaller fraction of neurons (~22%, 150 out of 681 neurons counted), mGluR1α was selectively targeted to axons (FIG. 6C, middle panel). This observation is consistent with previous studies suggesting the existence of an axonal targeting signal (RRK877-879) in mGluR1α C-terminus, which is normally masked by the distal C-terminus domain. Our results from NMDA-induced translocation indicated that calpain-mediated truncation could unmask the axon-targeting signal and thereby alter mGluR1α subcellular distribution. There were also a few neurons (~4.5%, 31 out of 681 neurons counted) where immunostaining appeared in dendrites. However, in contrast to the even distribution of wild-type mGluR1α in dendrites, the truncated mGluR1α formed large clusters (FIG. 7C, bottom panel).

Figure 8:
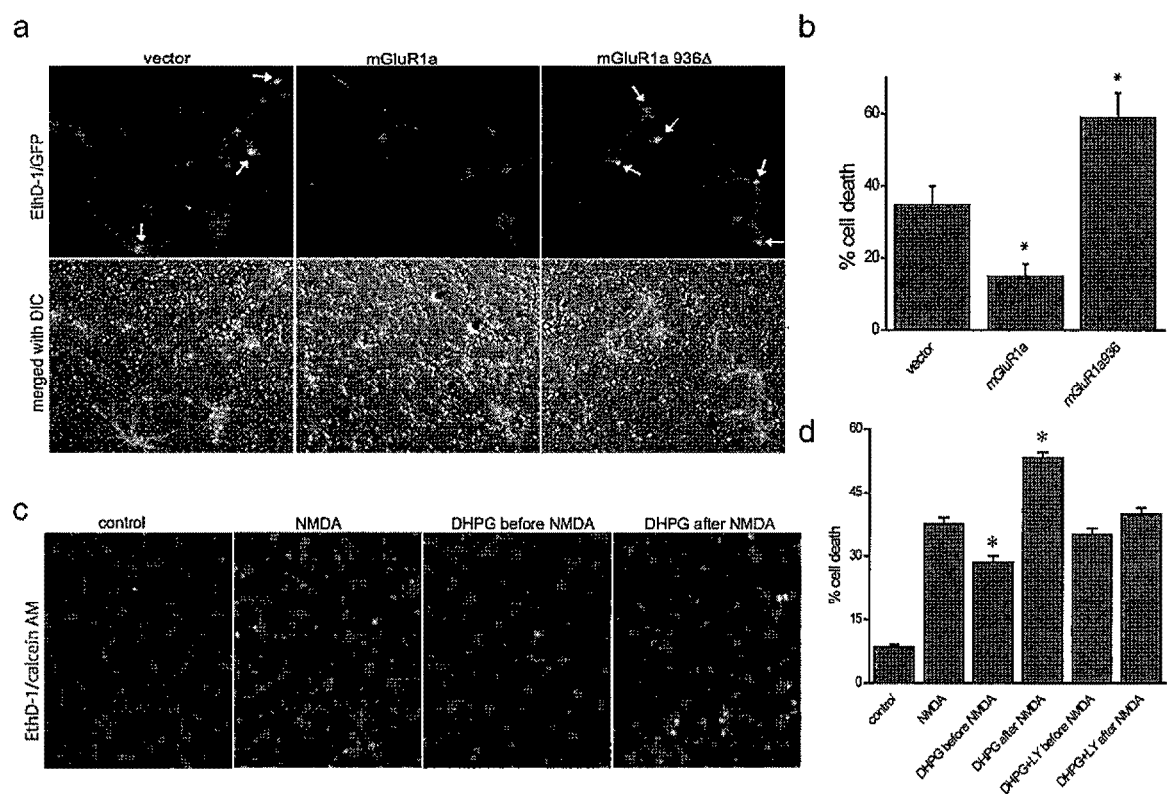
FIG. 8 shows the distinct roles of wild-type and truncated mGluR1α in excitotoxicity and interactions with NMDA receptor activation.

7. Distinct and Opposite Roles of Wild-Type and Truncated mGluR1α in Excitotoxicity FIG. 8 shows the distinct roles of wild-type and truncated mGluR1α in excitotoxicity and interactions with NMDA receptor activation. In FIGS. 8a and b, cortical neurons were co-transfected with green fluorescent protein (GFP) and vector DNA, myc-mGluR1α or myc-mGluR1α936Δ, respectively. Fourty-eight hours later, neurons were treated with 25 μM glutamate for 1 hour. Twelve hours later, neurons were stained with EthD-1 to label dead cells. Arrowheads in FIG. 8a indicate EthD-1 positive GFP-expressing neurons. * p<0.05. FIGS. 8c and d are representative photos and bar graphs showing differential roles of endogenous mGluR1 in neuronal toxicity before and after NMDA-induced truncation. Cortical neurons were treated as indicated and were stained with EthD-1 (for dead cells) and calcein AM (for live cells) 24 hours later. * p<0.001.

Calpain-mediated truncation of mGluR1α was only induced by toxic concentrations of NMDA. The downstream signaling pathways of mGluR1α, including release of intracellular calcium and activation of P13K-Akt, are both important for excitotoxicity. Therefore, we postulated that NMDA-induced truncation would alter the role of mGluR1α in neuronal toxicity. To test this possibility, we first co-transfected neurons with GFP and a control vector, wild-type mGluR1α or truncated mGluR1α respectively. Forty-eight hours later, neurons were treated with 25 μM glutamate for 1 hour. Twelve hours after treatment, neurons were stained with 0.5 µM EthD-1 for 10 minutes to label dead cells. The numbers of GFP-expressing neurons and EthD-1 positive GFP-expressing neurons on each 18×18 mm coverslip were counted to calculate the percentage of dead cells. As shown in FIGS. 8a and b, the toxic effects of glutamate treatment could readily be observed in most GFP-expressing neurons, which exhibited significant neurite retraction. In neurons co-transfected with control vector, 35% (n=9, on average, there were 405 GFP-expressing neurons counted on each coverslip) of GFP-expressing neurons were positive for EthD-1 staining and therefore had died. In neurons co-transfected with wild-type mGluR1α, only 15% of neurons (n=8, in average, there were 428 GFP-expressing neurons counted on each coverslip) were EthD-1 positive, an effect that was statistically different from that in neurons co-transfected with control vector ($p<0.01$, Student's t-test). In contrast, 59% of neurons co-transfected with mGluR1α936Δ (n=9, in average, there were 439 GFP-expressing neurons counted on each coverslip) were EthD-1 positive, an effect significantly higher than observed in neurons co-transfected with control vector ($p<0.05$, Student's t-test). We also tested the effects of higher concentrations of glutamate (50 and 100 µM respectively) and performed the staining 24 hours after glutamate treatment; however, under these conditions, GFP staining could only be observed in debris of neurites and was largely lost from cell bodies. Therefore it was difficult to determine the exact location of cell bodies and the live/dead ratios in those neurons. The opposing effects of wild-type and truncated mGluR1α indicated that wild-type and truncated mGluR1α have distinct roles in excitotoxicity.

We then tested whether calpain-mediated truncation of endogenous mGluR1α also alters its roles in excitotoxicity. We used NMDA to elicit mGluR1α truncation and evaluated the roles of mGluR1 in neuronal toxicity by applying DHPG before and after truncation. Fourteen DIV cortical neurons cultured on 18×18 mm coverslips were divided into 6 groups, which received the following treatments, respectively: 1) "Control": vehicle; 2) "NMDA": 100 µM NMDA for 1 hour; 3) "DHPG before NMDA": DHPG, 100 µM, for 1 hour, followed by 100 µM NMDA for 1 hour; 4) "DHPG after NMDA": NMDA, 100 µM, for 1 hour, followed by 100 µM DHPG for 1 hour; 5) "DHPG+LY before NMDA": 100 µM DHPG was co-applied with 100 µM LY367385 for 1 hour and followed by 100 µM NMDA for 1 hour; 6) "DHPG+LY after NMDA": NMDA 100 µM for 1 hour, followed by 100 µM DHPG co-applied with 100 µM LY367385. Twenty-four hours after treatment, all neurons were stained for 20 minutes with 0.5 µM EthD-1 to label dead cells and 2 µM Calcein AM to label live cells. After three washes with culture medium, coverslips were mounted and one microscopy photo was immediately taken from the center area of each coverslip. EthD-1 and Calcein AM positive cells on each photo were then counted. The percentage of cell death was calculated as the number of EthD-1 positive cell/(number of EthD-1 positive cell+number of Calcein AM positive cell)*100%. As shown in FIGS. 8c and d, "Control" had 8% cell death (n=12). In "NMDA", cell death rate increased to 37% (n=12), which was significantly higher than that in "Control" ($p<0.001$, Student's t-test) indicating the toxic activity of NMDA; 29% cell death was found in "DHPG before NMDA" (n=9), which was significantly lower than that of "NMDA" ($p<0.001$, Student's t-test) suggesting a neuroprotective effect of DHPG under this condition. This effect was completely blocked by co-applying LY367385 ("DHPG+LY before NMDA", 35% cell death, n=11; $p<0.05$ compared with "DHPG before NMDA"; $p=0.38$ compared with "NMDA", Student's t-test) indicating that it was mediated by mGluR1. "DHPG after NMDA" had 54% cell death (n=12), which was significantly higher than that of "NMDA" ($p<0.001$, Student's t-test), indicating a neurotoxic effect of DHPG treatment under this condition. Similarly, this toxic effect was completely blocked by co-applying LY367385 ("DHPG+LY after NMDA", 40% cell death, n=9; $p<0.001$ compared with "DHPG after NMDA"; $p=0.27$ compared with "NMDA", Student's t-test) indicating that this effect was mediated by mGluR1. The opposing effects of DHPG before and after NMDA-induced truncation thus demonstrate the distinct roles of whole length and truncated endogenous mGluR1α.

8. The Role of the Positive Feedback Loop in NMDA Toxicity

Figure 9:
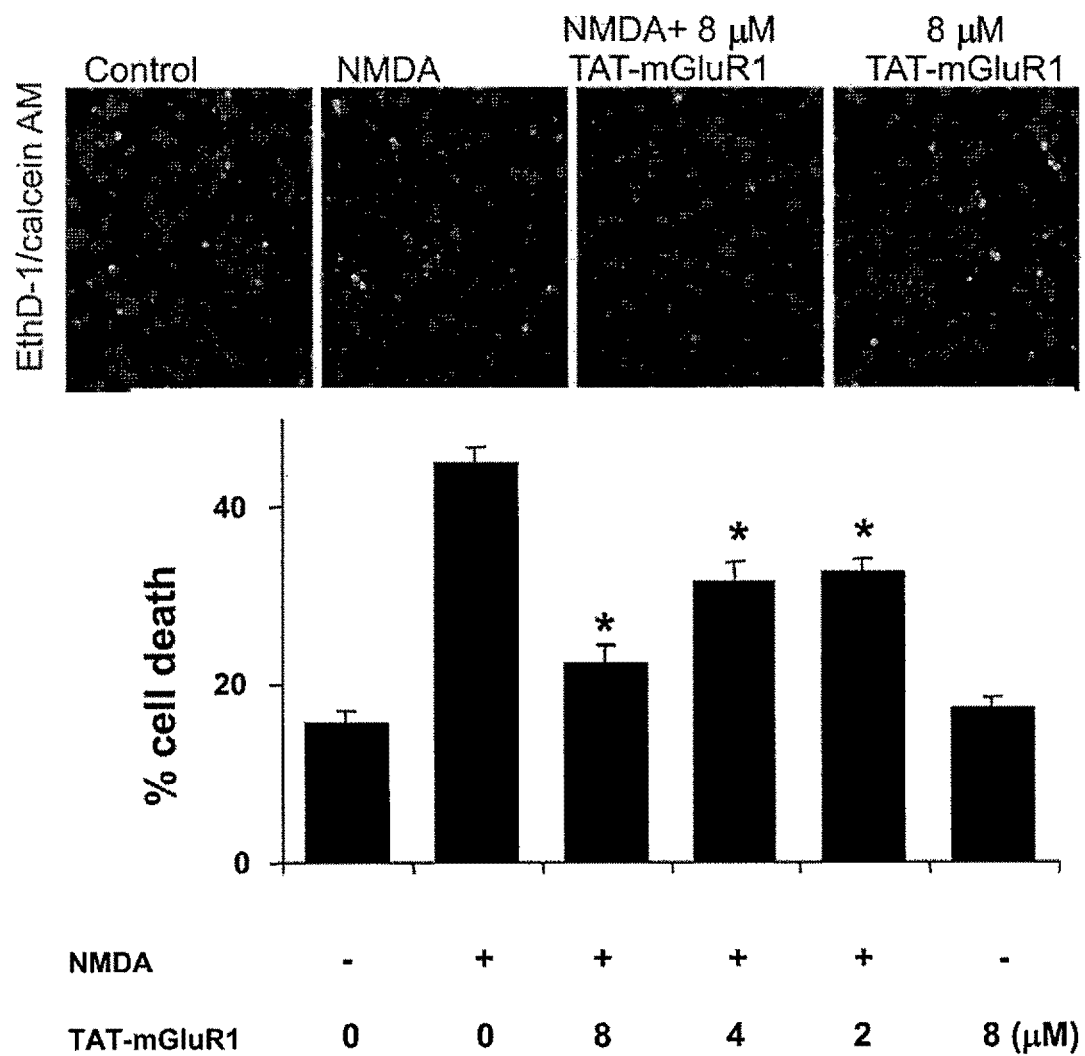
FIG. 9 shows blockade of NMDA neurotoxicity by the tat-mGluR1 peptide.

FIG. 9 shows blockade of NMDA neurotoxicity by the tat-mGluR1 peptide. In this figure, cultured neurons were pretreated with the tat-peptide for 90 min. They were then treated with NMDA (50 µM) for 1 h. They were analyzed 12 h later by live/dead cell assay (0.5 µM EthD-1 and 2 µM Calcein AM).

The top portion of FIG. 9 shows representative images of cultured neurons under various conditions. The bottom portion of FIG. 9 shows the dose-response for the tat-mGluR1 peptide. Remarkably, the tat-mGluR1 peptide almost completely prevented NMDA-mediated neurotoxicity at a concentration of 8 µM.

9. In vivo Activation of the Positive Feedback Loop

Figure 10:
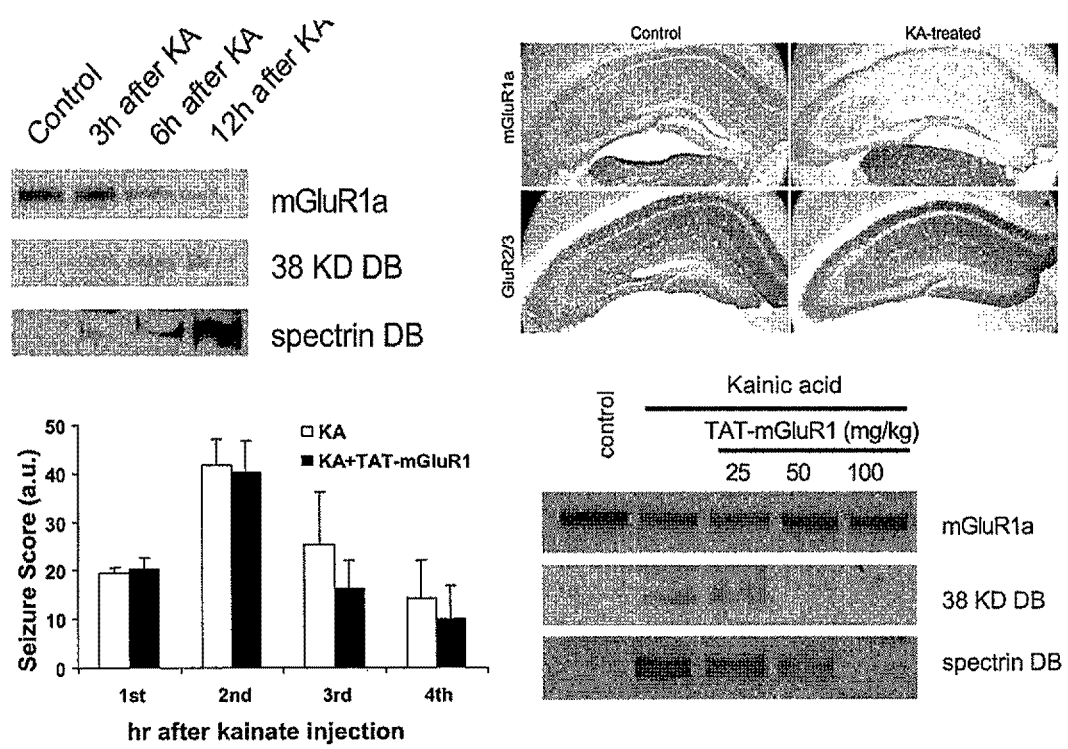
FIG. 10 shows in vivo truncation of the C-terminal domain of mGluR1α following KA injection and protection by the tat-mGluR1 peptide.

FIG. 10 shows the result when adult mice (FVB) were injected with kainic acid (30 mg/kg, s.c.) and sacrificed at the indicated time (top left) or 12 h (top and bottom right) later. The tat-peptide was injected i.p. 90 min before kainic acid injection. Note that the peptide had no effect on seizure intensity (bottom left).

Figure 11:
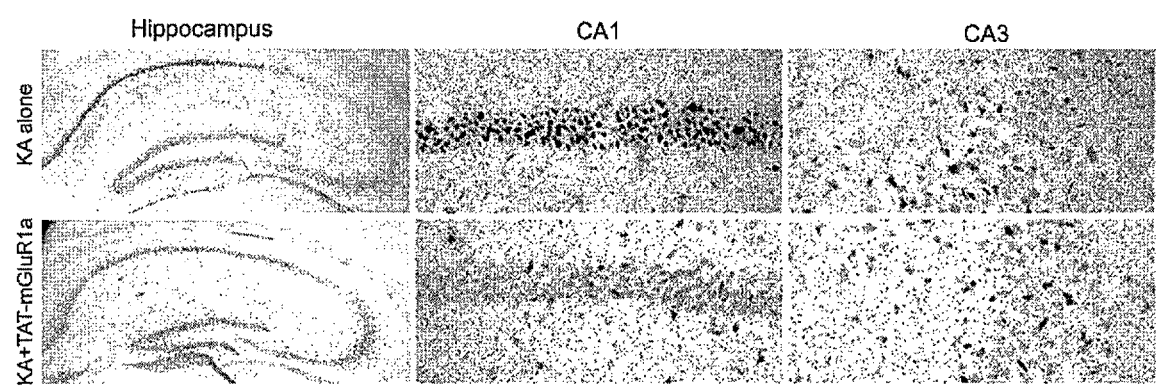
FIG. 11 shows that the tat-mGluR1 peptide protects hippocampal neurons from KA-induced toxicity.

FIG. 11 shows the result when adult mice were injected with kainic acid (30 mg/kg, s.c.) 90 min after an injection of saline (top row) or the tat-mGluR1 peptide (100 mg/kg, i.p.). They were sacrificed after 7 days and brains processed for silver staining, a marker of cell damage. Note the heavy labeling of the pyramidal cell layer in the KA alone group. This effect was dramatically reduced in animals treated with the tat-mGluR1 peptide.

The objective of this set of experiments was to verify that the feedback mechanism of the present invention could take place in vivo and participate in excitotoxicity. We used the kainic acid model of excitotoxicity, as this model has been widely used to study the mechanisms underlying in vivo excitotoxicity (Wang et al. Mol Neurobiol 31:3-16, 2005). Mice were injected with kainic acid and sacrificed at different times after injection. Levels of mGluR1α were determined in hippocampus with both Western blots and immunohistochemistry (FIG. 10). The results clearly indicated that mGluR1 was rapidly truncated following kainic acid injection and that administration of the tat-mGluR1 peptide significantly reduced its truncation.

The effect of the tat-mGluR1 peptide on kainic acid-induced neuronal damage was also evaluated. As previously shown in the literature, kainic acid treatment resulted in marked damage to CA1 pyramidal neurons and some damage in CA3 pyramidal neurons (FIG. 11). Treatment with the tat-mGluR1 peptide significantly reduced the extent of neuronal damage. Note that the tat-mGluR1 peptide did not influence the severity or duration of the seizures resulting from systemic injection of kainic acid, thereby eliminating the possibility that the neuroprotective effects of the peptide are simply due to the reduction in seizure activity (bottom left panel in FIG. 10).

10. Truncation Blocker is Not Necessarily Calpain Inhibitor

As previously mentioned, calpain inhibitors were previously shown to exert neuroprotective effects in some models of neurodegeneration, and it could be argued that the effects of the tat-mGluR1 peptide we observed were due to some calpain inhibitor effects of the peptide. However, the inventors of the present invention have discovered that this is not likely the case. In particular, when brain membranes were treated with purified calpain in the presence of calcium, truncation of both mGluR1 and spectrin was observed. When the tat-mGluR1 peptide was added, it only prevented mGluR1 truncation and not spectrin degradation, indicating that the tat-mGluR1 peptide does not function as a general calpain inhibitor. The inventors believe that the peptide acts as a calpain substrate competing with mGluR1 for calpain. The selective protection of tat-mGluR1 has the advantage that it may act as a selective blocking agent without disrupting calpain's other enzymatic activities. Thus, a blocking agent of the present invention will have the advantage of having reduced side-effect profile than calpain inhibitors.

11. Tat-mGluR1 is Neuroprotective in OGD-induced Neuronal Injury in Cultured Hippocampal Slices We used a well-known in vitro stroke model, combined oxygen/glucose deprivation in cultured hippocampal slices, to test the idea that the mechanism we have proposed, i.e., calpain-mediated truncation of mGluR1, accounts for neuronal death in stroke. Furthermore, we tested the neuroprotective effects of the tat-mGluR1 peptide in this stroke model. In this model, cultured hippocampal slices are treated for various periods of time (30-60 min) by changing the cultured medium to a medium without glucose and replacing the normal air/5% $CO_2$ with nitrogen. After this period of time, slices are returned to normal glucose-containing medium and exposed to air/5% CO2 and are cultured for again various periods of time. Cell death is evaluated by measuring the amount of LDH release in the medium at various times, as well as by the extent of Propidium Iodide (PI) uptake in the cells (LDH release in the medium is an index of membrane damage, as LDH is a cytoplasmic enzyme; likewise, PI is generally not taken up by cells, except if the cell membrane is severely compromised).

Figure 12:
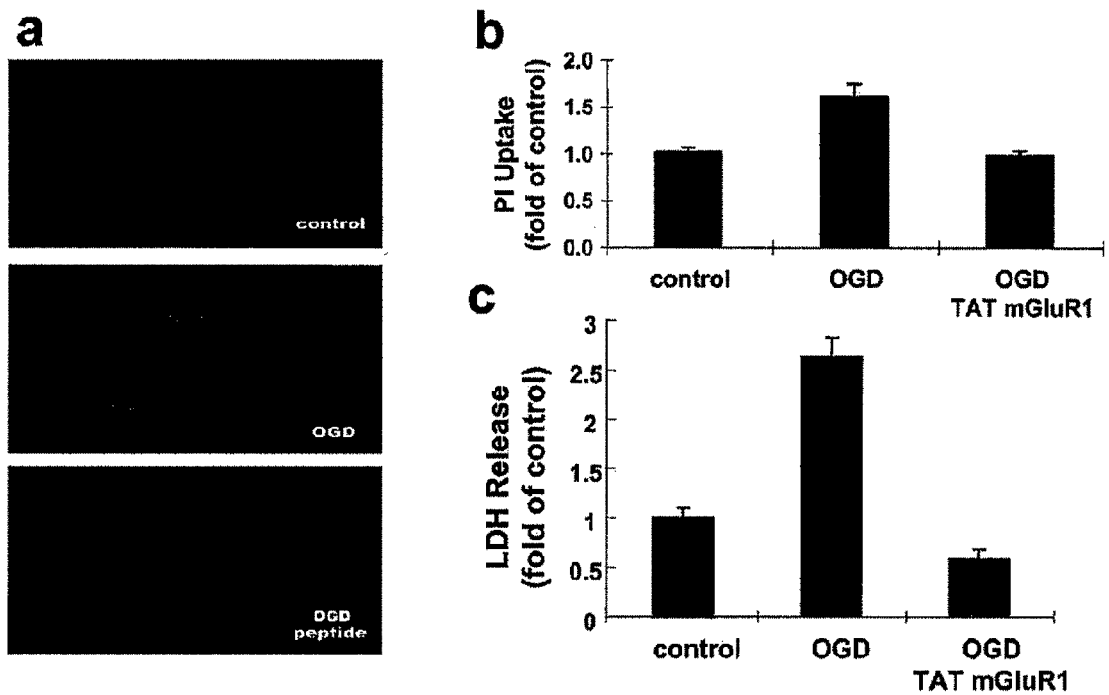
FIG. 12 shows effects of tat-mGluR1 peptide on OGD (oxygen-glucose deprivation)-induced cell death in cultured hippocampal slices. Cultured slices were subjected to OGD for 30 min, and returned to normal glucose and oxygen conditions for 24 h. Neuronal damage was assessed by the propidium iodide (PI) uptake method, which labels damaged cells (a, b), and by LDH release in culture medium (c).

We first showed that, while control slices exhibited very low levels of PI staining, OGD-treated slices exhibited massive staining throughout the hippocampus, especially in CA1&CA3 24 h after a 30 min episode of OGD (FIG. 12a). Treatment of cultured slices with tat-mGluR1 (10 µM) for 3 h before and during OGD (30 min) provided complete neuroprotection when assessed with LDH release or PI uptake at 3 h and 24 h (FIGS. 12b and c) after OGD.

Figure 13:
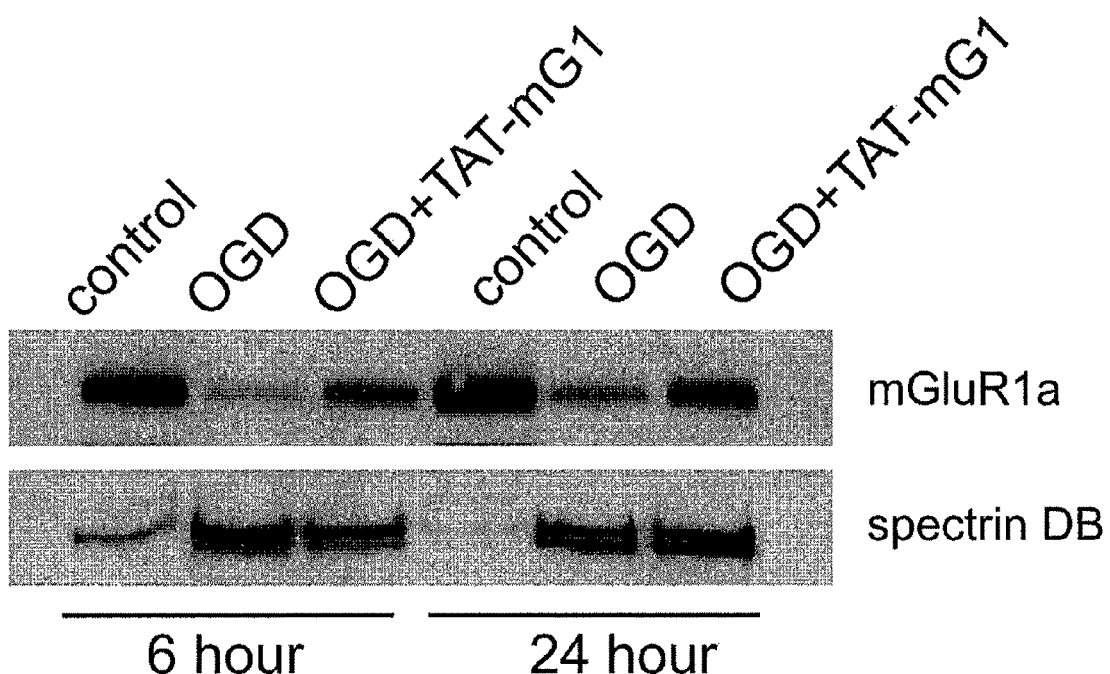
FIG. 13 shows effects of OGD in cultured hippocampal slices on mGluR1 and spectrin degradation. Cultured hippocampal slices were subjected to 50-min OGD and returned to normal culture condition for another 6 or 24 hours. The immunoblots showed a significant cleavage of mGluR1α after OGD that could be partially restored by the TAT-mGluR1α fusion peptide.

With longer periods of OGD, we showed that mGluR1 was truncated and the presence of the calpain-mediated truncated form of mGluR1 as well as the typical pattern of spectrin degradation indicated that calpain activation was responsible for the truncation (FIG. 13). Furthermore, the tat-mGluR1 peptide almost completely blocked OGD-induced mGluR1 truncation (FIG. 13).

Thus, these results indicate that in this in vitro stroke model, mGluR1 is truncated by calpain, and that the tat-mGluR1 peptide is neuroprotective.

12. Ischemia Induced Calpain-mediated mGluR1 Truncation

Figure 14:
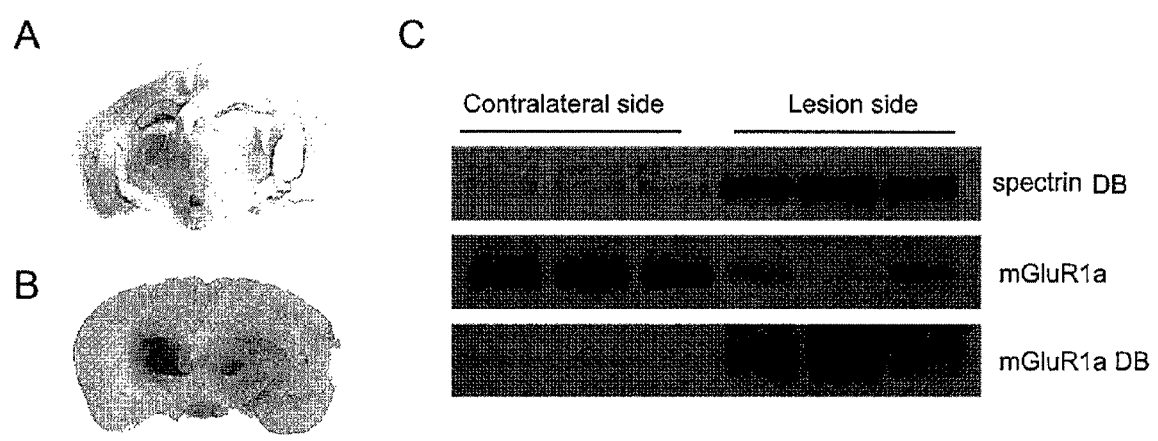
FIG. 14 shows mGluR1 truncation in mice brain in a stroke model. 2-month-old mice received a unilateral occlusion of common carotid artery combined with a 45-minute hypoxia (using the protocol as described in Adhami et al., Am J Pathol 169(2):566-583, 2006). Brain tissue was collected 24 hours after the hypoxia. (A) Nissl staining showing the brain lesion induced by ischemia (the right side is the occlusion side). (B) Immunostaining for mGluR1α with the antibody against the C-terminus of mGluR1α. The highest immunoreactivity of mGluR1α was found in the thalamus region, which is significantly reduced in the lesion side (right side). (C) Immunoblots of hippocampal tissues from 3 mice with ischemia. Levels of native mGluR1α in the lesion side are significantly reduced while levels of the calpain-mediated degradation product of mGluR1 are increased in parallel with the increase in the 145 kDa spectrin degradation band.

For an in vivo stroke model, we used a modified Levine/Vannucci model developed by Dr. Guanghong Liao (Research Scientist in Dr Xiaoning Bi's lab at Western University of Health Sciences) and her colleagues at the Children's Hospital at Cincinnati. In this model, adult mice are subjected to a unilateral occlusion of the common carotid artery combined with a 45 min hypoxia. Brain tissues were collected 24 h after the hypoxia (FIG. 14). By comparing the lesion side to the contralateral (control) side, it is apparent that mGluR1 is truncated and the appearance of the mGluR1 degradation product in parallel with the increase in spectrin degradation clearly indicates that the degradation is mediated by calpain.

Throughout this application, various references are referred to. Disclosures of these publications in their entireties are hereby incorporated by reference into this application to more fully describe the state of the art to which this invention pertains.

What is claimed is:

1. A composition comprising a peptide or a peptidomimetic thereof that inhibits the C-terminal domain truncation of mGluR1α by calpain, wherein the peptide is 14 amino acids in length and contains a sequence that is at least 70% homologous to VIKPLTKSYQGSGK (SEQ ID NO: 1); and a pharmaceutically acceptable carrier.

2. The composition of claim 1, wherein the peptide contains a sequence that is at least 80% homologous to VIKPLTKSYQGSGK (SEQ ID NO: 1).

3. The composition of claim 2, wherein the peptide contains a sequence that is at least 90% homologous to VIKPLTKSYQGSGK (SEQ ID NO: 1).

4. The composition of claim 3, wherein the peptide contains a sequence that is at least 95% homologous to VIKPLTKSYQGSGK (SEQ ID NO: 1).

5. The composition of claim 4, wherein the peptide is VIKPLTKSYQGSGK (SEQ ID NO 1).

6. The composition of claim 1, wherein the peptide of the composition contains a sequence selected from VIKPLTKG-GQGSGK (SEQ ID NO: 2), VIKPLTK-dS-dY-QGSGK (SEQ ID NO: 3), or VIKPLTK-dA-dF-QGSGK (SEQ ID NO: 4).

7. The composition of claim 1, wherein the composition further contains YGRKKRRQRRRVIKPLTKSYQGSGK (SEQ ID NO: 5), RRRQRRKKRGYVIKPLTKSYQGSGK (SEQ ID NO: 6), VIKPLTKSYQGSGKYGRKKRRQRRR (SEQ ID NO: 7), or

```
CYGRKKRRQRRR
|
CVIKPLTKSYQGSGK,
``` defined as a peptide of residues 1 to 12 of SEQ ID NO: 8 joined to a peptide of residues 13-27 of SEQ ID NO: 8.

8. The composition of claim 1, which contains a peptidomimetic of SEQ ID NO: 1, wherein said peptidomimetic contains a peptide nucleic acid subsequence.

9. A method of inhibiting the C-terminal domain truncation of mGluR1α by calpain, comprising contacting calpain in the presence of mGluR1α with the composition of claim 1, thereby inhibiting the C-terminal domain truncation of mGluR1α by the calpain.

* * * * *